United States Patent
McInnes et al.

(10) Patent No.: US 11,162,083 B2
(45) Date of Patent: Nov. 2, 2021

(54) PEPTIDE BASED INHIBITORS OF RAF KINASE PROTEIN DIMERIZATION AND KINASE ACTIVITY

(71) Applicant: UNIVERSITY OF SOUTH CAROLINA, Columbia, SC (US)

(72) Inventors: Campbell McInnes, Irmo, SC (US); Chad Beneker, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 16/441,054

(22) Filed: Jun. 14, 2019

(65) Prior Publication Data

US 2019/0382738 A1    Dec. 19, 2019

Related U.S. Application Data

(60) Provisional application No. 62/829,781, filed on Apr. 5, 2019, provisional application No. 62/684,959, filed on Jun. 14, 2018.

(51) Int. Cl.

| C07K 7/08  | (2006.01) |
| C12N 9/12  | (2006.01) |
| C07K 14/82 | (2006.01) |
| A61K 38/00 | (2006.01) |

(52) U.S. Cl.
CPC .......... *C12N 9/12* (2013.01); *C07K 7/08* (2013.01); *C07K 14/82* (2013.01); *A61K 38/00* (2013.01)

(58) Field of Classification Search
None
See application file for complete search history.

(56) References Cited

U.S. PATENT DOCUMENTS

| 7,291,601 B1 | 11/2007 | Chae et al. |
| 7,432,260 B2 | 10/2008 | Wang et al. |
| 7,449,544 B2 | 11/2008 | Zheleva et al. |
| 7,576,091 B2 | 8/2009 | McInnes et al. |
| 7,897,605 B2 | 3/2011 | Wang et al. |
| 8,566,072 B2 | 10/2013 | McInnes et al. |
| 9,175,357 B2 | 11/2015 | McInnes et al. |
| 9,328,139 B2 | 5/2016 | McInnes et al. |
| 9,376,465 B2 | 6/2016 | McInnes et al. |
| 9,982,015 B2 | 5/2018 | McInnes et al. |
| 10,067,131 B2 | 9/2018 | McInnes et al. |
| 2003/0036628 A1 | 2/2003 | Zheleva et al. |
| 2003/0086929 A1 | 5/2003 | Tso et al. |
| 2003/0129656 A1 | 7/2003 | Park et al. |
| 2003/0171904 A1 | 9/2003 | Lewis et al. |
| 2003/0187220 A1 | 10/2003 | Park et al. |
| 2003/0225527 A1 | 12/2003 | Antonysamy et al. |
| 2004/0176301 A1 | 9/2004 | Zheleva et al. |
| 2004/0229290 A1 | 11/2004 | Hellinga et al. |
| 2005/0192300 A1 | 9/2005 | Wang et al. |
| 2005/0196808 A1 | 9/2005 | Yaffe et al. |
| 2005/0264628 A1 | 11/2005 | McInnes et al. |
| 2006/0040997 A1 | 2/2006 | McInnes et al. |
| 2006/0281687 A1 | 12/2006 | Andrews et al. |
| 2006/0293245 A1 | 12/2006 | Zheleva et al. |
| 2008/0070843 A1 | 3/2008 | Livnah et al. |
| 2008/0132484 A1 | 6/2008 | McInnes et al. |
| 2008/0167385 A1 | 7/2008 | Kontopidis et al. |
| 2008/0287439 A1 | 11/2008 | Wang et al. |
| 2009/0215805 A1 | 8/2009 | Wood et al. |
| 2010/0004141 A1 | 1/2010 | Khvorova et al. |
| 2012/0202970 A1 | 8/2012 | McInnes et al. |
| 2013/0289240 A1 | 10/2013 | McInnes et al. |
| 2014/0296484 A1 | 10/2014 | McInnes et al. |
| 2014/0316107 A1 | 10/2014 | McInnes et al. |
| 2016/0011195 A1 | 1/2016 | McInnes et al. |
| 2017/0218018 A1 | 8/2017 | McInnes et al. |
| 2017/0283445 A1 | 10/2017 | McInnes et al. |

FOREIGN PATENT DOCUMENTS

| GB | 2369823 | 6/2002 |
| WO | WO 2004/067000 | 8/2004 |
| WO | WO 2005/005438 | 1/2005 |
| WO | WO 2005/040802 | 5/2005 |
| WO | WO 2005/042565 | 5/2005 |

(Continued)

OTHER PUBLICATIONS

Röring et al., "Distinct requirement for an intact dimer interface in wild-type, V600E and kinase-dead B-Raf signaling", The EMBO Journal, (2011), 2629-2647 (Year: 2011).*

Ganz, "Defensins: Antimicrobial Peptides of Innate Immunity", Nature Reviews Immunology, (2003) 710-720 (Year: 2003).*

Buku et al. "Mast Cell Degranulating (MCD) Peptide Analogs with Reduced Ring Structure", Journal of Protein Chemistry, 1992:275-280 (Year: 1992).*

Agianian, et al. "Current Insights of BRAF Inhibitors in Cancer" *J. Med. Chem.* 61 (2018) pp. 5775-5793.

Andrews, et al. "REPLACE: A strategy for iterative design of cyclin-binding groove inhibitors" *ChemBioChem* 7 (2006) pp. 1909-1915.

(Continued)

*Primary Examiner* — Lianko G Garyu

(74) *Attorney, Agent, or Firm* — Dority & Manning, P.A.

(57) ABSTRACT

Herein are described peptide-based compositions for modifying Raf kinase protein Dimerization. These compositions, treatments, and methods of use are directed to peptides that display a binding affinity for the dimer interface of a Raf kinase protein, methods for modifying Raf kinase dimerization, and methods for inhibiting tumor growth. An embodiment of the disclosure is a peptide generated by modifying an ordered sequence chosen from SEQ ID NO: 1 which corresponds to amino acids 503-521 of B-Raf kinase. The peptides disclosed herein include a modification to an ordered sequence of amino acids derived from SEQ ID NO: 1 that can improve or otherwise alter binding affinity of the peptide to the dimer interface.

20 Claims, 15 Drawing Sheets

Specification includes a Sequence Listing.

(56) References Cited

FOREIGN PATENT DOCUMENTS

| WO | WO 2005/052147 | 6/2005 |
|----|----------------|--------|
| WO | WO 2005/108421 | 11/2005 |

OTHER PUBLICATIONS

Bernal, et al. "Reactivation of the p53 tumor suppressor pathway by a stapled p53 peptide" *J Am Chem Soc* 129 (2007) pp. 2456-2457.

Bollag, et al. "Clinical efficacy of a RAF inhibitor needs broad target blockade in BRAF-mutant melanoma" *Nature* 467 (2010) pp. 596-599.

Brummer, et al. "Inducible gene deletion reveals different roles for B-Raf and Raf-1 in B-cell antigen receptor signaling" *EMBO J* 21 (2002) pp. 5611-5622.

Chatterjee, et al. "N-methylation of peptides and proteins: An important element for modulating biological functions" *Angew Chem* 52 (2013) pp. 254-269.

Chatterjee, et al. "Synthesis of N-methylated cyclic peptides" *Nat Protoc* 7 (2012) pp. 432-444. (Abstract only).

Chmielecki, et al. "Comprehensive Genomic Profiling of Pancreatic Acinar Cell Carcinomas Identifies Recurrent RAF Fusions and Frequent Inactivation of DNA Repair Genes" *Cancer Discov* 4 (2014) pp. 1398-1405.

Chou, et al. "Prediction of β-turns" *Biophys J* 26 (1979) pp. 367-383.

Collaborative Computational Project, No. 4 "The CCP4 suite: Programs for protein crystallography" *Acta Cryst.* D50 (1994) pp. 760-763.

Cox, et al. "The Raf inhibitor paradox: Unexpected consequences of targeted drugs" *Cancer Cell* 17 (2010) pp. 221-223.

Diedrich, et al. "Discrete cytosolic macromolecular BRAF complexes exhibit distinct activities and composition" *EMBO J* 36 (2017) pp. 646-663.

Durrant, et al. "Targeting the Raf kinases in human cancer: The Raf dimer dilemma" *Br J Cancer* 118 (2018) pp. 3-8.

Eisenhardt, et al. "Phospho-proteomic analyses of B-Raf protein complexes reveal new regulatory principles" *Oncotarget* 7 (2016) pp. 26628-26652.

Freeman, et al. "Effects of Raf dimerization and its inhibition on normal and disease-associated Raf signaling" *Mol Cell* 49 (2013) pp. 751-758.

Garnett, et al. "Guilty as charged: B-RAF is a human oncogene" *Cancer Cell* 6 (2004) pp. 313-319.

Giordanetto, et al. "Macrocyclic drugs and clinical candidates: What can medicinal chemists learn from their properties?" *J Med Chem* 57 (2014) pp. 278-295.

Haigis, et al. "Differential effects of oncogenic K-Ras and N-Ras on proliferation, differentiation and tumor progression in the colon" *Nat Genet* 40 (2008) pp. 600-608.

Hatzivassiliou, et al. "RAF inhibitors prime wild-type RAF to activate the MAPK pathway and enhance growth" *Nature* 464: (2010) pp. 431-435.

Haug, et al. "Metadherin exon 11 skipping variant enhances metastatic spread of ovarian cancer" *Int J Cancer* 136 (2015) pp. 2328-2340.

Heidorn, et al "Kinase-dead BRAF and oncogenic RAS cooperate to drive tumor progression through CRAF" *Cell* 140 (2010) pp. 209-221.

Herr, et al. "B-Raf Inhibitors Induce Epithelial Differentiation in BRAF-Mutant Colorectal Cancer Cells" *Cancer Res* 75 (2015) pp. 216-229.

Herr, et al. "A novel MCF-10A line allowing conditional oncogene expression in 3D culture" *Cell Commun Signal* 9:17 (2011) pp. 1-13.

Hingorani, et al. "Trp53$^{R172H}$ and Kras$^{G12D}$ cooperate to promote chromosomal instability and widely metastatic pancreatic ductal adenocarcinoma in mice" *Cancer Cell* 7 (2005) pp. 469-483.

Hu, et al. "Allosteric Activation of Functionally Asymmetric RAF Kinase Dimers" *Cell* 154 (2013) pp. 1036-1046.

Kamata, et al. "BRAF inactivation drives aneuploidy by deregulating CRAF" *Cancer Res* 70 (2010) pp. 8475-8486.

Kaplan, et al. "Hyperactivation of MEK-ERK 1/2 signaling and resistance to apoptosis induced by the oncogenic B-RAF inhibitor, PLX4720, in mutant N-RAS melanoma cells" *Oncogene* 30 (2011) pp. 366-371.

Karoulia, et al. "An Integrated Model of RAF Inhibitor Action Predicts Inhibitor Activity against Oncogenic BRAF Signaling" *Cancer Cell* 30 (2016) pp. 485-498.

Köhler, et al. "Activation loop phosphorylation regulates B-Raf in vivo and transformation by B-Raf mutants" *EMBO J* 35 (2016) pp. 143-161.

Kontopidis, et al. "Truncation and optimisation of peptide inhibitors of cyclin-dependent kinase 2-cyclin a through structure-guided design" *ChemMedChem* 4 (2009) pp. 1120-1128.

Kontopidis, et al. "Differential binding of inhibitors to active and inactive CDK2 provides insights for drug design" *Chem Biol* 13 (2006) pp. 201-211.

Kordes, et al. "Cooperation of BRAF$^{F595L}$ and mutant HRAS in histiocytic sarcoma provides new insights into oncogenic BRAF signaling" *Leukemia* 30 (2016) pp. 937-946. (Abstract only).

Lakowicz, J.R. "Principles of Fluorescence Spectroscopy" *Springer Science & Business Media* (2006).

Lavoie, et al. "Regulation of RAF protein kinases in ERK signaling" *Nat Rev Mol Cell Biol* 16 (2015) pp. 281-298.

Lavoie, et al. "Inhibitors that stabilize a closed RAF kinase domain conformation induce dimerization" *Nat Chem Biol* 9 (2013) pp. 428-436.

Leslie, A.G.W. "Recent changes to the MOSFLM package for processing film and image plate data" *Joint CCP4 + ESF-EAMCB Newsletter on Protein Crystallography* (1992).

Liu, et al. "Optimization of Non-ATP Competitive CDK/Cyclin Groove Inhibitors through REPLACE—Mediated Fragment Assembly" *J Med Chem* 56 (2013) pp. 1573-1582.

Mcinnes, et al. "Targeting subcellular localization through the polo-box domain: non-ATP competitive inhibitors recapitulate a PLK1 phenotype" *Molecular Cancer Therapeutics* 11 (2012) pp. 1683-1692.

Mcinnes, C. "Progress in the development of Non-ATP competitive Protein Kinase Inhibitors for Oncology" *Annual Reports in Medicinal Chemistry* 47 (2012) pp. 459-474. (Abstract only).

Michaloglou, et al. "BRAF$^{E600}$ in benign and malignant human tumours" *Oncogene* 27 (2008) pp. 877-895.

Misawa, et al. "Rapid and high-sensitivity cell-based assays of protein-protein interactions using split click beetle luciferase complementation: An approach to the study of G-protein-coupled receptors" *Anal Chem* 82 (2010) pp. 2552-2560.

Nielsen, et al. "Orally Absorbed Cyclic Peptides" *Chem Rev* 117 (2017) pp. 8094-8128.

Nieto, et al. "A Braf kinase-inactive mutant induces lung adenocarcinoma" *Nature* 548 (2017) pp. 239-243.

Otwinowski, et al. "Processing of x-ray diffraction data collected in oscillation mode" *Methods Enzymol.* 276 (1997) pp. 307-326. (Abstract only).

Papaneophytou, et al. "Quantification of the effects of ionic strength, viscosity, and hydrophobicity on protein-ligand binding affinity" *ACS Med Chem Lett* 5 (2014) pp. 931-936.

Pflugrath, J. "The finer things in X-ray diffraction data collection" *Acta Cryst.* D55 (1999) pp. 1718-1725.

Poulikakos, et al. "RAF inhibitor resistance is mediated by dimerization of aberrantly spliced BRAF$^{V600E}$" *Nature* 480 (2011) pp. 387-390.

Poulikakos, et al. "RAF inhibitors transactivate RAF dimers and ERK signalling in cells with wild-type BRAF" *Nature* 464 (2010) pp. 427-430.

Premnath, et al. "Iterative Conversion of Cyclin Binding Groove Peptides into Druglike CDK Inhibitors with Antitumor Activity" *J Med Chem* 58 (2015) pp. 433-442.

Qin, et al. "Identification of a novel family of BRAF$^{V600E}$ inhibitors" *J Med Chem* 55 (2012) pp. 5220-5230.

Rajakulendran, et al. "A dimerization-dependent mechanism drives RAF catalytic activation" *Nature* 461 (2009) pp. 542-545.

(56) References Cited

OTHER PUBLICATIONS

Röring, et al. "Distinct requirement for an intact dimer interface in wild-type, V600E and kinase-dead B-Raf signaling" *EMBO J* 31 (2012) pp. 2629-2647.
Roskoski, Jr., R. "Classification of molecule protein kinase inhibitors based upon the structures of their drug-enzyme complexes" *Pharmacol Res* 103 (2016) pp. 26-48.
Ross, et al. "The distribution of BRAF gene fusions in solid tumors and response to targeted therapy" *Int J Cancer* 138 (2016) pp. 881-890.
Samatar, et al. "Targeting RAS-ERK signalling in cancer: promises and challenges" *Nat Rev Drug Discov* 13 (2014) pp. 928-942.
Selt, et al. "Establishment and application of a novel patient-derived KIAA1549:BRAF-driven pediatric pilocytic astrocytoma model for preclinical drug testing" *Oncotarget* 8 (2017) pp. 11460-11479.
Shaw, et al. "Kinases and pseudokinases: Lessons from RAF" *Mol Cell Biol* 34 (2014) pp. 1538-1546.
Sherr, C.J. "Cancer cell cycles" *Science* 274 (1996) pp. 1672-1677.
Sievert, et al. "Paradoxical activation and RAF inhibitor resistance of BRAF protein kinase fusions characterizing pediatric astrocytomas" *Proc Natl Acad Sci USA* 110 (2013) pp. 5957-5962.
Sur, et al. "A panel of isogenic human cancer cells suggests a therapeutic approach for cancers with inactivated p53" *Proc Natl Acad Sci USA* 106(10)(2009) pp. 3964-3969.
Thevakumaran, et al. "Crystal structure of a BRAF kinase domain monomer explains basis for allosteric regulation" *Nat Struct Mol Biol* 22 (2015) pp. 37-43.
Thota, et al. "Trametinib in the treatment of melanoma" *Expert Opin Biol Ther* 15 (2015) pp. 735-747. (Abstract only).
Verdine, et al. "Stapled peptides for intracellular drug targets" *Methods Enzymol* 503 (2012) pp. 3-33. (Abstract only).
Villar, et al. "How proteins bind macrocycles" *Nat Chem Biol* 10 (2014) pp. 723-731.
Walensky, et al. "A stapled BID BH3 helix directly binds and activates BAX" *Mol Cell* 24 (2006) pp. 199-210.
Walensky, et al. "Activation of apoptosis in vivo by a hydrocarbon-stapled BH3 helix" *Science* 305 (2004) pp. 1466-1470.
Wargo, et al. "Universes Collide: Combining Immunotherapy with Targeted Therapy for Cancer" *Cancer Discov* 4(12) (2014) pp. 1377-1386.
Weinberg, et al. "The Atypical Kinase RIOK1 Promotes Tumor Growth and Invasive Behavior" *EBioMedicine* 20 (2017) pp. 79-97.
Wimmer, et al. "Partner exchange: Protein-protein interactions in the Raf pathway" *Trends Biochem Sci* 35 (2010) pp. 660-668.
Wu, et al. "Increased BRAF heterodimerization is the common pathogenic mechanism for noonan syndrome-associated RAF1 mutants" *Mol Cell Biol* 32 (2012) pp. 3872-3890.
Yaktapour, et al. "BRAF inhibitor-associated ERK activation drives development of chronic lymphocytic leukemia" *J Clin Invest* 124 (2014) pp. 5074-5084.
Yang, et al. "DNA damage and homologous recombination signaling induced by thymidylate deprivation" *Biochem Pharmacol* 76 (2008) pp. 987-996.
Yao, et al. "Tumours with class 3 BRAF mutants are sensitive to the inhibition of activated RAS" *Nature* 548 (2017) pp. 234-238.
Yao, et al. "BRAF Mutants Evade ERK-Dependent Feedback by Different Mechanisms that Determine Their Sensitivity to Pharmacologic Inhibition" *Cancer Cell* 28 (2015) pp. 370-383.
Yuan, et al. "Development of siRNA payloads to target KRAS-mutant cancer" *Cancer Discov* 4 (2014) pp. 1182-1197.

\* cited by examiner

| ID | BRAF Residues | Sequence | Kd (μM) |
|---|---|---|---|
| 1 | 503-521 | GVLRKTRHVNILLFMGYST | 3.84 ±0.32 |
| 2 | 503-521 R509H, L515G, M517W | GVLRKTHHVNILGFWGYST | NB |
| 3 | scrambled | GRINKGRHTFLLVVMTYSL | 2.96 ± 0.18 |
| 4 | 503-521 L505A | GVARKTRHVNILLFMGYST | 3.89 ±0.53 |
| 5 | 503-521 R506E | GVLEKTRHVNILLFMGYST | 1.09 ±0.29 |
| 6 | 503-521 R506L | GVLLKTRHVNILLFMGYST | 0.54 ±0.11 |
| 7 | 503-521 T508D | GVLRKDRHVNILLFMGYST | 2.2 ±0.83 |
| 8 | 503-521 T508A | GVLRKARHVNILLFMGYST | 2.8 ±0.29 |
| 9 | 503-521 H510F | GVLRKTRFVNILLFMGYST | NB |
| 10 | 503-521 V511A | GVLRKTRHANILLFMGYST | 4.75 ±1.7 |
| 11 | 503-521 L514A | GVLRKTRHVNIALFMGYST | 9.8 ±1.6 |
| 12 | 503-521 L515I | GVLRKTRHVNILIFMGYST | 4.1 ±1.1 |
| 13 | 503-521 L515homoleucine | GVLRKTRHVNIL(HL)FMGYST | 1.25 ±0.36 |
| 14 | 503-521 F516D | GVLRKTRHVNILLDMGYST | NB |
| 15 | 503-518 | GVLRKTRHVNILLFMG | 1.88 ±0.36 |

FIG. 1

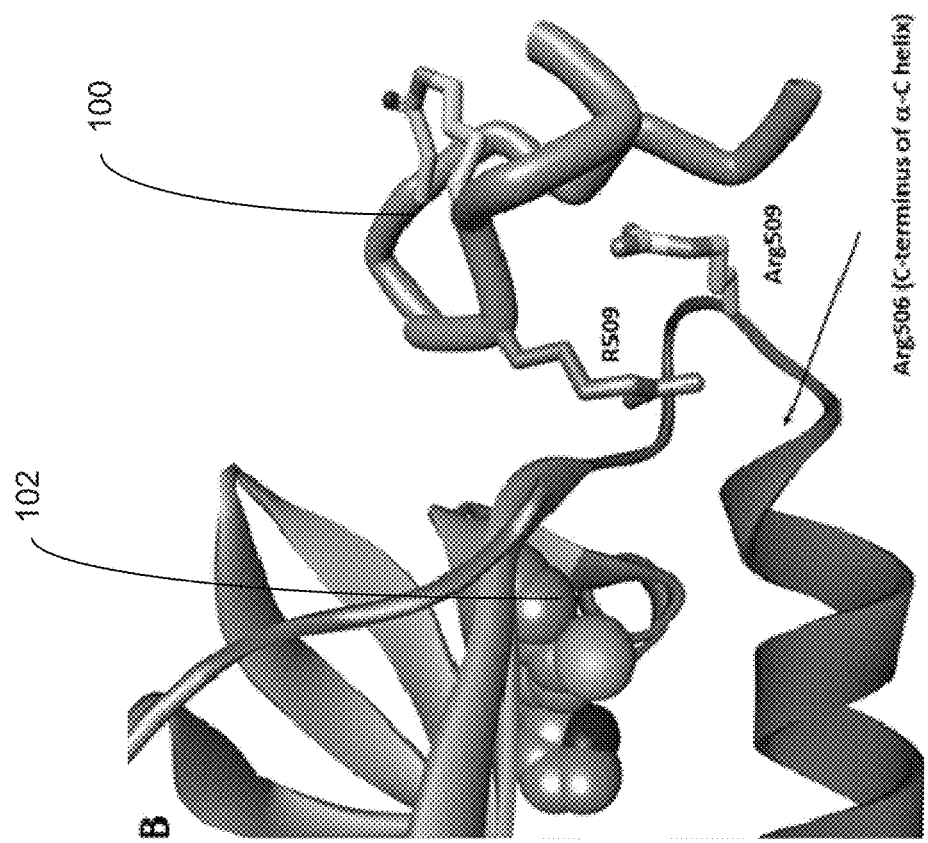
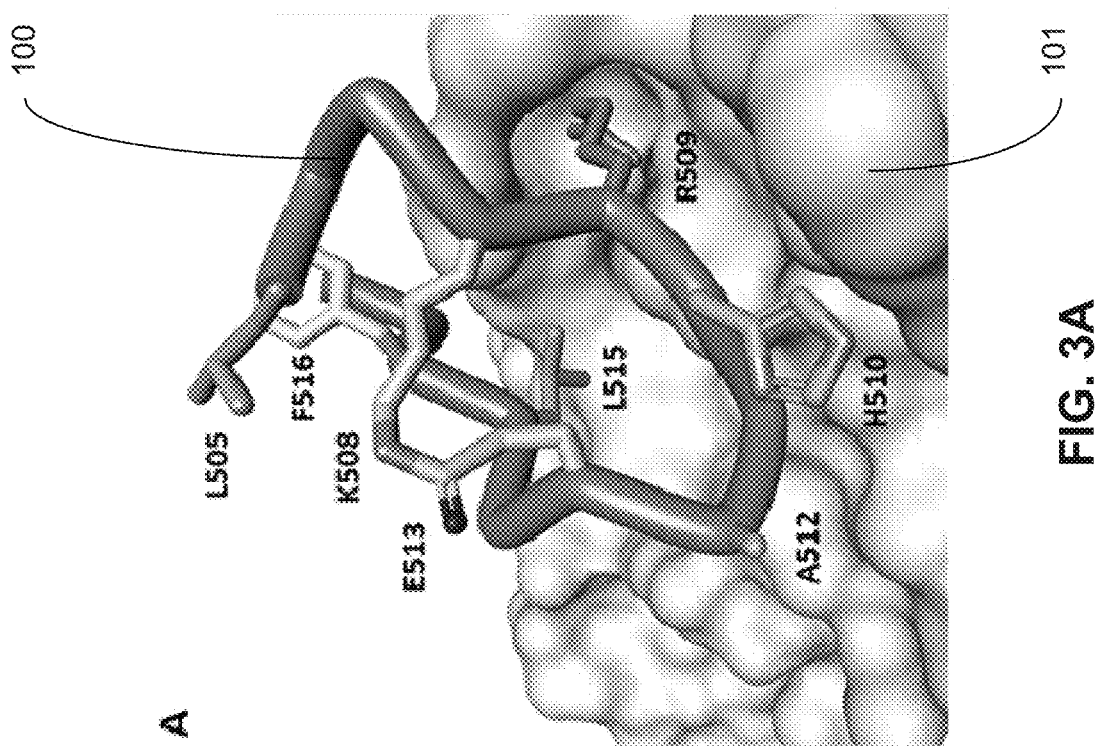
FIG. 3B
FIG. 3A

| SEQ ID NO | B-Raf Residues | Sequence | Kd (µM) |
|---|---|---|---|
| 16 | 504-517 | VLRKTRHVNILLFM | 5.75 ± 1.2 |
| 17 | 504-518 | VLRKTRHVNILLFMG | 0.13 ±0.040 |
| 18 | 504-518 | VLRKTRHVNILLFMG-NH₂ | 0.48 ±0.091 |
| 19 | 504-518 | Ac-VLRKTRHVNILLFMG | 0.8 ±0.083 |
| 20 | 504-518 L515homoleucine | VLRKTRHVNIL{HL}FMG | 0.49 ±0.16 |
| 21 | 504-518 L505A | VARKTRHVNILLFMG | 0.45 ±0.03 |
| 22 | 504-518 R506A | VLAKTRHVNILLFMG | 0.36 ±0.03 |
| 23 | 504-518 K507A | VLRATRHVNILLFMG | NT |
| 24 | 504-518 R509A | VLRKTAHVNILLFMG | 2.4 ±0.35 |
| 25 | 504-518 H510A | VLRKTRAVNILLFMG | 2.7 ±0.4 |
| 26 | 504-518 N512A | VLRKTRHVAILLFMG | NB |
| 27 | 504-518 I513A | VLRKTRHVNALLFMG | 2.69± 0.35 |
| 28 | 504-518 L514A | VLRKTRHVNIALFMG | 1.02 ±0.14 |
| 29 | 504-518 F516A | VLRKTRHVNILLAMG | 0.57 ±0.08 |
| 30 | 504-518 M517A | VLRKTRHVNILLFAG | 0.54 ±0.15 |
| 31 | 505-518 | LRKTRHVNILLFMG | 0.19 ±0.13 |
| 32 | 505-518 R506L | LLKTRHVNILLFMG | 0.55 ±0.105 |

FIG. 8

Table 3. Structure-activity of cyclic BRAF Dimer Interface Peptides

| SEQ ID NO | B-Raf Residues | Sequence | Kd (µM) |
|---|---|---|---|
| 33 | cyclo 504-518 L505C, F516C | VCRKTRHVNILLCM | 0.36 ±0.32 |
| 34 | 508-513 T508O, N512A, I513E | LRKORHVAELLFMG | NB |
| 35 | cyclo 508-513 T508O, I513E | LRKORHVNELLFMG | 0.78 ±0.10 |
| 36 | cyclo 508-513 T508O, N512A, I513E | LRKORHVAELLFMG | 0.46 ±0.04 |
| 37 | cyclo 508-513 T508K, I513E | LRKKRHVNELLFMG | 1.89±0.33 |
| 38 | cyclo 508-513 T508K, N512A, I513E | LRKKRHVAELLFMG | 0.061±0.01 |

FIG. 9

| SEQ ID NO | Purity | Column Dimensions | Method |
|---|---|---|---|
| 1 | >90% | 4.6 x 250 mm | 5-65% acetonitrile/water/0.1%TFA/25 min |
| 2 | >90% | 4.6 x 250 mm | 5-65% acetonitrile/water/0.1%TFA/25 min |
| 3 | >90% | 4.6 x 250 mm | 5-65% acetonitrile/water/0.1%TFA/25 min |
| 4 | >90% | 4.6 x 250 mm | 5-65% acetonitrile/water/0.1%TFA/25 min |
| 5 | >90% | 4.6 x 250 mm | 5-65% acetonitrile/water/0.1%TFA/25 min |
| 6 | >90% | 4.6 x 250 mm | 5-65% acetonitrile/water/0.1%TFA/25 min |
| 7 | >90% | 4.6 x 250 mm | 5-65% acetonitrile/water/0.1%TFA/25 min |
| 8 | >90% | 4.6 x 250 mm | 5-65% acetonitrile/water/0.1%TFA/25 min |
| 9 | >90% | 4.6 x 250 mm | 5-65% acetonitrile/water/0.1%TFA/25 min |
| 10 | >90% | 4.6 x 250 mm | 5-65% acetonitrile/water/0.1%TFA/25 min |
| 11 | >90% | 4.6 x 250 mm | 5-65% acetonitrile/water/0.1%TFA/25 min |
| 12 | >90% | 4.6 x 250 mm | 5-65% acetonitrile/water/0.1%TFA/25 min |
| 13 | >90% | 4.6 x 250 mm | 5-65% acetonitrile/water/0.1%TFA/25 min |
| 14 | >90% | 4.6 x 250 mm | 5-65% acetonitrile/water/0.1%TFA/25 min |
| 15 | >90% | 4.6 x 250 mm | 5-65% acetonitrile/water/0.1%TFA/25 min |
| 16 | >90% | 4.6 x 250 mm | 5-65% acetonitrile/water/0.1%TFA/25 min |
| 17 | >90% | 4.6 x 250 mm | 5-65% acetonitrile/water/0.1%TFA/25 min |
| 18 | >90% | 4.6 x 250 mm | 5-65% acetonitrile/water/0.1%TFA/25 min |
| 19 | >90% | 4.6 x 250 mm | 5-65% acetonitrile/water/0.1%TFA/25 min |
| 20 | >90% | 4.6 x 250 mm | 5-65% acetonitrile/water/0.1%TFA/25 min |
| 21 | >90% | 4.6 x 250 mm | 5-65% acetonitrile/water/0.1%TFA/25 min |
| 22 | >90% | 4.6 x 250 mm | 5-95% acetonitrile/water/0.1%TFA/35 min |
| 23 | >90% | 4.6 x 250 mm | 5-65% acetonitrile/water/0.1%TFA/25 min |
| 24 | >90% | 4.6 x 250 mm | 5-65% acetonitrile/water/0.1%TFA/25 min |
| 25 | >90% | 4.6 x 250 mm | 5-65% acetonitrile/water/0.1%TFA/25 min |
| 26 | >90% | 4.6 x 250 mm | 5-65% acetonitrile/water/0.1%TFA/25 min |
| 27 | >90% | 4.6 x 250 mm | 5-65% acetonitrile/water/0.1%TFA/25 min |
| 28 | >90% | 4.6 x 250 mm | 5-65% acetonitrile/water/0.1%TFA/25 min |
| 29 | >90% | 4.6 x 250 mm | 5-65% acetonitrile/water/0.1%TFA/25 min |
| 30 | >90% | 4.6 x 250 mm | 5-65% acetonitrile/water/0.1%TFA/25 min |
| 31 | >90% | 4.6 x 250 mm | 5-65% acetonitrile/water/0.1%TFA/25 min |
| 32 | >90% | 4.6 x 250 mm | 5-95% acetonitrile/water/0.1%FA/30 min |
| 33 | >90% | 4.6 x 250 mm | 5-65% acetonitrile/water/0.1%TFA/25 min |
| 34 | 96% | 4.6 x 250 mm | 5-95% acetonitrile/water/0.1%FA/40 min |
| 35 | >95% | 4.6 x 250 mm | 5-95% acetonitrile/water/0.1%FA/30 min |
| 36 | 87% | 4.6 x 250 mm | 5-95% acetonitrile/water/0.1%FA/30 min |
| 37 | >90% | 4.6 x 250 mm | 5-95% acetonitrile/water/0.1%FA/30 min |
| 38 | >90% | 4.6 x 250 mm | 5-95% acetonitrile/water/0.1%FA/30 min |

FIG. 10a

| SEQ ID NO | FlowRate | Retention Time | Theoretical MW | Observed MW |
|---|---|---|---|---|
| 1 | 1ml/min | 20.3 | 2205.6 | 2205.0 |
| 2 | 1ml/min | 19.3 | 2185.5 | 2186.1 |
| 3 | 1ml/min | 20.7 | 2205.6 | 2205.9 |
| 4 | 1ml/min | 17.1 | 2163.5 | 2163.3 |
| 5 | 1ml/min | 19.9 | 2178.6 | 2178.2 |
| 6 | 1ml/min | 19.4 | 2162.6 | 2162.4 |
| 7 | 1ml/min | 18.2 | 2219.6 | 2219.4 |
| 8 | 1ml/min | 17.7 | 2175.6 | 2175.3 |
| 9 | 1ml/min | 20.2 | 2215.7 | 2215.3 |
| 10 | 1ml/min | 18.3 | 2177.6 | 2177.2 |
| 11 | 1ml/min | 17.0 | 2163.6 | 2163.4 |
| 12 | 1ml/min | 18.6 | 2205.6 | 2205.4 |
| 13 | 1ml/min | 20.1 | 2219.6 | 2219.4 |
| 14 | 1ml/min | 17.7 | 2173.6 | 2173.3 |
| 15 | 1ml/min | 17.7 | 1854.3 | 1853.9 |
| 16 | 1ml/min | 17.7 | 1740.2 | 1739.9 |
| 17 | 1ml/min | 17.0 | 1797.2 | 1797.5 |
| 18 | 1ml/min | 18.9 | 1796.2 | 1796.1 |
| 19 | 1ml/min | 14.8 | 1839.3 | 1839.7 |
| 20 | 1ml/min | 13.1 | 1781.2 | 1781.2 |
| 21 | 1ml/min | 15.0 | 1755.2 | 1755.2 |
| 22 | 1ml/min | 15.5 | 1712.1 | 1712.4 |
| 23 | 1ml/min | 15.9 | 1740.1 | 1740.2 |
| 24 | 1ml/min | 19.4 | 1712.1 | 1712.0 |
| 25 | 1ml/min | 13.6 | 1731.2 | 1731.5 |
| 26 | 1ml/min | 17.5 | 1754.2 | 1754.2 |
| 27 | 1ml/min | 17.8 | 1755.2 | 1755.3 |
| 28 | 1ml/min | 16.4 | 1755.2 | 1755.5 |
| 29 | 1ml/min | 13.9 | 1721.1 | 1721.3 |
| 30 | 1ml/min | 15.3 | 1737.1 | 1737.2 |
| 31 | 1ml/min | 18.8 | 1698.1 | 1697.5 |
| 32 | 1ml/min | 16.7 | 1655.1 | 1655.0 |
| 33 | 1ml/min | 17.5 | 1684.1 | 1683.5 |
| 34 | 1ml/min | 17.6 | 1683.1 | 1682.0 |
| 35 | 1ml/min | 17.2 | 1707.0 | 1708.0 |
| 36 | 1ml/min | 17.4 | 1664.0 | 1664.0 |
| 37 | 1ml/min | 17.7 | 1722.1 | 1724.0 |
| 38 | 1ml/min | 18.2 | 1679.1 | 1680.0 |

FIG. 10b

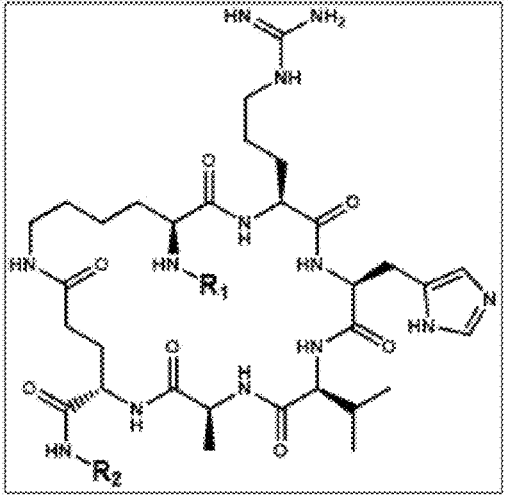
| R1 | R2 | Structure | CAS# of precursor | Interaction Energy | NCap IE Total including lysine | Capping group contribution only |
|---|---|---|---|---|---|---|
| - | - | Lys | N/A | -80.2 | -9.0 | - |
| Ncap1 | LLFMG-NH2 | 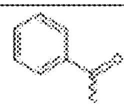 | 65-85-0 | -87.6 | -15.9 | -6.9 |
| Ncap2 | LLFMG-NH2 | 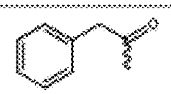 | 103-82-2 | -89.6 | -16.4 | -7.4 |
| Ncap3 | LLFMG-NH2 | 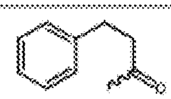 | 501-52-0 | -85.7 | -13.0 | -4.0 |
| Ncap4 | LLFMG-NH2 | 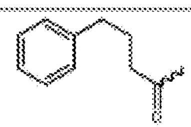 | 1821-12-1 | -86.8 | -14.0 | -5.0 |
FIG. 12

| Mol_ID | MolWeight | DESCRIPTION | Kd (ITF) (µM) |
|---|---|---|---|
| 6254 | 1403.71 | N1-TRHVNILLFMG | 0.05 ±0.0055 |
| 6257 | 1325.67 | LRKTRHVNI-C2 | 0.02 ±0.0095 |

| Capping Group Name | Capping Group Structure |
|---|---|
| N1 | |
| C2 | |

FIG. 14

PEPTIDE BASED INHIBITORS OF RAF KINASE PROTEIN DIMERIZATION AND KINASE ACTIVITY

CROSS REFERENCE TO RELATED APPLICATION

This application claims filing benefit of U.S. Provisional Application Ser. No. 62/829,781, having a filing date of Apr. 5, 2019, and of U.S. Provisional Application Ser. No. 62/684,959, having a filing date of Jun. 14, 2018, each of which is incorporated herein by reference in its entirety.

FEDERAL RESEARCH STATEMENT

This invention was made with Government support under Grant No. R21 CA191899, awarded by National Institutes of Health. The Government has certain rights in the invention.

SEQUENCE LISTING

The instant application contains a Sequence Listing which has been filed electronically in ASCII format and is hereby incorporated by reference in its entirety. Said ASCII copy, created on Jul. 29, 2019, is named USC-616_Sequence List.txt and is 13,562 bytes in size.

BACKGROUND

Tumors with mutant RAF kinases and mutant RAS enzymes represent some of the deadliest forms of cancer, including metastatic melanomas and pancreatic cancers. These two protein families are involved in the transduction of extracellular growth signals to the nucleus to regulate cell proliferation and differentiation, and both proteins are often involved in a pathway affected in tumor formation. Considerable efforts in drug discovery have been invested in modifying the signal transduction pathways associated with RAF kinases (A-Raf, B-Raf, and Raf-1/C), yet there is still a need for further efforts as drug resistance and heterogeneity of tumor cells can pose challenges to single drug treatments.

Oncogenic RAS signaling occurs in about 30% of all human cancers and triggers homo- or hetero-dimerization of Raf-kinases that is critical for several aspects of signal propagation through downstream MEK and ERK kinases. Despite intense efforts, pharmacologic inhibition of RAS proteins themselves and inhibition of their downstream effector kinases has so far been unsuccessful in treating RAS-driven tumors. Indeed, ATP-competitive Raf inhibitors cause the so-called paradoxical ERK activation in this context, and therefore, should not be used to treat RAS mutant tumors. This phenomenon is caused by drug-bound B-Raf molecules that promote activation of drug-free Raf protomers in the context of excessive Ras signaling via an allosteric mechanism.

There is a huge, unmet medical need for improved treatment options for patients worldwide. For instance, while drugs that inhibit B-Raf, called paradox breakers, have been developed, such drugs have proven ineffective in tumors that have acquired mutant forms of the kinase. What are needed in the art are materials that can exhibit effectiveness against RAF kinases, and particularly against mutant forms of these proteins.

SUMMARY

Embodiments of the disclosure are directed to peptides that display a binding affinity for the dimer interface of a Raf kinase protein, methods for modifying Raf kinase dimerization, and methods for inhibiting tumor growth. An embodiment of the disclosure is a peptide generated by modifying an ordered sequence chosen from SEQ ID NO: 1. SEQ ID NO: 1 corresponds to amino acids 503-521 of B-Raf kinase and the peptide displays a binding affinity ($K_d$) of about 3.84 µM for the dimer interface of B-Raf. The peptides disclosed herein include a modification to an ordered sequence of amino acids derived from SEQ ID NO: 1 that can improve or otherwise alter binding affinity of the peptide to the dimer interface.

Another embodiment of the disclosure is a method for modifying Raf kinase dimerization by delivering a peptide to the protein. By modifying Raf kinase dimerization, embodiments of the disclosure can alter or decrease Raf kinase activity. Additional embodiments utilize the decreased kinase activity to provide methods for inhibiting tumor growth. Raf kinase activity is activated in several types of tumors, and embodiments of the disclosure also provide methods for modifying tumor growth that include delivering a peptide generated by modifying an ordered sequence from SEQ ID NO: 1 to a tumor or a target cell.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which:

FIG. 1 illustrates a table providing the SEQ ID NOs of exemplary peptides. The table includes a description of modifications made to the starting B-Raf peptide (SEQ ID NO:1) along with the resulting peptide sequences showing substitutions in bold. A measured dissociation constant $K_d$ is also provided for each peptide.

FIG. 3A illustrates the structure of SEQ ID NO: 38 bound to B-Raf.

FIG. 3B illustrates the Dimer Interface (DI) showing the interaction between the SEQ ID NO: 38 and B-Raf. R509 (peptide) forms an anti-parallel binding mode with Arg509 (B-Raf) as observed from the crystal structure.

FIG. 8 illustrates a table providing the SEQ ID NOs of exemplary peptides. The table includes a description of modifications made to the starting B-Raf peptide (SEQ ID NO: 1) along with the resulting peptide sequences showing substitutions in bold. A measured dissociation constant $K_d$ is provided for each peptide.

FIG. 9 illustrates a table providing the SEQ ID NOs of exemplary peptides. The table includes a description of modifications made to the starting B-Raf peptide (SEQ ID NO: 1) along with the resulting peptide sequences showing substitutions in bold. A measured dissociation constant $K_d$ is provided for each peptide.

FIG. 10a illustrates a table displaying the conditions used in an LCMS analysis including column dimensions and method.

FIG. 10b illustrates a table displaying the conditions used in the LCMS analysis including the flow rate, retention time, theoretical molecular weight and observed molecular weight for SEQ ID NOs 1-38.

FIG. 12 illustrates arrangements of chemical structures for example peptide-based inhibitors developed using the REPLACE strategy in accordance with example embodiments of the disclosure. "LLFMG" is disclosed as SEQ ID NO: 44.

FIG. 14 illustrates arrangements of chemical structures for example peptide-based inhibitors developed using the REPLACE strategy in accordance with example embodiments of the disclosure. FIG. 14 discloses SEQ ID NOS 45-46, respectively, in order of appearance.

Figures 2A, 2B:
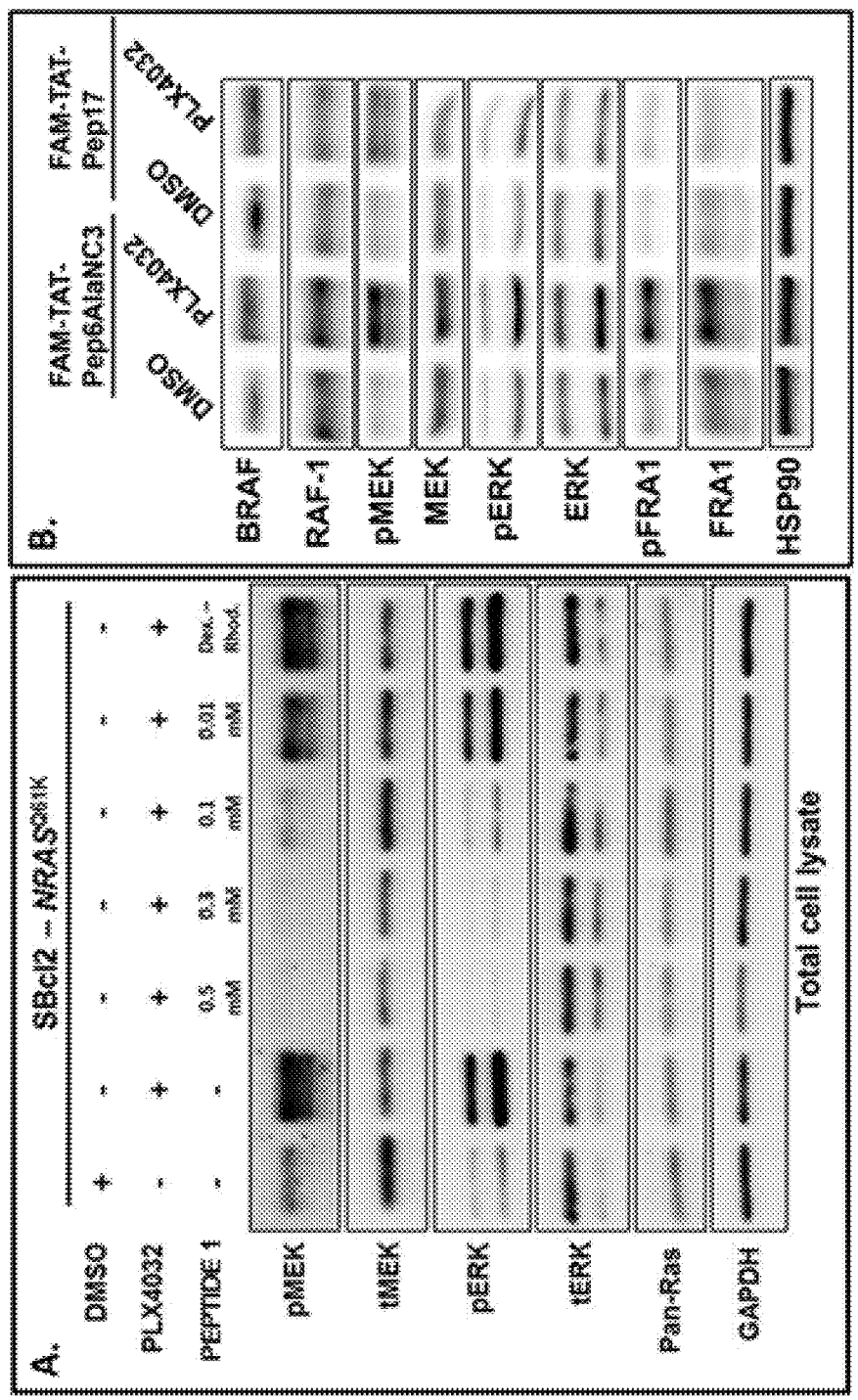
FIGS. 2A-2B illustrate Western blot gels. The top portion shows the different conditions (DMSO, PLX4032, and Peptide 1) and the gel portion shows the stain for different antibodies specific to the proteins on the left (e.g., pMEK, tMEK, pERK, tERK, Pan-Ras, and GAPDH).

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment may be used in another embodiment to yield a still further embodiment.

In general, disclosed herein are peptides that display a binding affinity for the dimer interface of a Raf kinase protein, methods for forming the peptides, and methods for using the peptides. By modifying dimerization, Raf kinase activity can be inhibited or reduced, for instance by allosteric binding.

An embodiment of the disclosure is a peptide that includes a modification to an ordered sequence of at least 5 amino acids from SEQ ID NO: 1. In these embodiments, the peptide displays a binding affinity for at least part of the dimer interface of a Raf kinase protein. SEQ ID NO: 1 includes B-Raf residues 503-521 and has the following amino acid sequence:

GVLRKTRHVNILLFMGYST   SEQ ID NO: 1

As used herein, an ordered sequence should be interpreted as a sequence of amino acids that remains substantially in the order of a reference sequence (e.g. SEQ ID NO: 1). The use of substantially in the order can be determined in many ways and generally connotates that the ordered sequence does not refer to a scrambled or reordered form of the reference sequence. Further, the ordered sequence includes a core sequence of 2 or more adjacent amino acids selected from the reference sequence. For embodiments of the disclosure, a modification is applied to alter the ordered sequence.

The disclosed peptides include a modification to an ordered sequence of at least 5 amino acids from SEQ ID NO: 1, the ordered sequence having a core sequence of 2 or more adjacent amino acids. In some embodiments, the core sequence will include at least one of R509, H510, or V511 of SEQ ID NO: 1. In an embodiment, a core sequence can include at least the R509 and the H510 of SEQ ID NO:1 or can include at least the H510 and the V511 of SEQ ID NO: 1. In an exemplary embodiment, the core sequence can correspond to residues R509 to V511 from SEQ ID NO: 1 (i.e. RHV). In other embodiments, the core sequence can be larger; for instance, the core sequence can correspond to residues V511 to T515 of SEQ ID NO: 1, residues G503 to H510 of SEQ ID NO: 1, residues G513 to L514 of SEQ ID NO: 1, residues G501 to G518 of SEQ ID NO: 1, or residues T508 to I513 of SEQ ID NO: 1.

Generally, the ordered sequence can include amino acids from the beginning, end, or complete length of SEQ ID NO: 1 (e.g., SEQ ID NOs: 4-15). In certain embodiments, the ordered sequence can include amino acids from the middle of SEQ ID NO: 1 (e.g., SEQ ID NOs: 16-32). In these examples, the ordered sequence is shown as the sequence of B-Raf residues, and the modification is shown after the ordered sequence (e.g., SEQ ID NO: 22 shows B-Raf residues 504-518 and modification R506A).

Certain embodiments of the disclosure include a peptide having an ordered sequence of more than 5 amino acids corresponding to SEQ ID NO: 1. In these embodiments, the composition can include a peptide that has at least 6, 7, 8, 9, 10, 12, 14, 16, 18 or 19 amino acids in an ordered sequence corresponding to SEQ ID NO: 1.

In embodiments of the disclosure, the peptide includes a modification to the ordered sequence. For instance, a portion of the ordered sequence of amino acids can include one or more modifications, which can encompass additions, deletions and/or substitutions to the amino acid residues. As an example, a peptide can include an ordered sequence corresponding to B-Raf residues 507-518 having a core sequence R509 to N512 of SEQ ID NO: 1 with internal deletions that do not impact the core sequence, e.g. KTRHVNILLFMG (SEQ ID NO: 42)>>KRHVNLLFMG (SEQ ID NO: 43). As another example, the peptide can include an ordered sequence corresponding to B-Raf residues 504-518 having a core sequence H510 to V511 with the substitution R506A (SEQ ID NO: 22).

In such embodiments, the modification can include an amino acid substitution where at least one of the amino acids of the ordered sequence is substituted for a different amino acid. As an example, the ordered sequence can include residues 503-521 of SEQ ID NO: 1 and the peptide can include a substitution of arginine at the 506 position for glutamic acid (i.e., R506E). Thus, the peptide can have the sequence: GVLEKTRHVNILLFMGYST (SEQ ID NO: 5).

Modifications can also include an amino acid insertion. For example, the ordered sequence can correspond to SEQ ID NO: 1 and the amino acid alanine could be inserted before the 503 position, between the 503 and 504 position, or after the 521 position to produce, respectively: AGVLEKTRHVNILLFMGYST (SEQ ID NO: [[1i]]39), GAVLEKTRHVNILLFMGYST (SEQ ID NO: [[2i]]40), and GVLEKTRHVNILLFMGYSTA (SEQ ID NO: [[3i]] 41).

There are many natural amino acids, which occur as L-isomers in most living organisms; however, embodiments of the disclosure are not limited to only L-amino acids and can include modifications that substitute D-amino acids or other non-proteinogenic amino acids that are not naturally encoded by humans or any other organism. Herein, unless specifically referenced as a D-amino acid (i.e., the amino acid identifier followed by (d)), reference to a generic amino acid indicates the L-amino acid.

In embodiments of the disclosure, the peptide can include an ornithine substitution to SEQ ID NO: 1. In some embodiments, the peptide may only include one or more amino acid substitutions of a human proteinogenic amino acids selected from the following group: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. In still other embodiments, the modification can include a combination of a non-proteinogenic amino acid substitution and a human proteinogenic amino acid substitution.

In an embodiment of the disclosure, the peptide having a modification can include substituting 2 or more amino acids from the ordered sequence for alternative amino acids. As an example, the 2 or more amino acid substitutions can include at least the substitutions: alanine for asparagine N512A and glutamic acid for isoleucine I513E as evidenced in SEQ ID NOs: 34, 36, and 38. As another example, the 2 or more amino acid substitutions can include at least the substitutions cysteine for leucine L505C and cysteine for phenylalanine F516C as evidenced in SEQ ID NO: 33.

Generally, the peptide can include a modification to a portion of the ordered sequence that can include one or more of the following amino acid substitutions: L505A, L505C, R506E, R506L, T508D, T508A, T5080, T508K, H510F, H510H(d), H510V, H510L, V511A, N512A, 1513E, L514A, L515I, L515 homoleucine, F516C, M517S, M517T, M517N and F516D. In particular, this list of modifications is not meant to constrain the embodiments described herein. As noted above, alternative substitutions may be practiced without departing from the spirit and scope of this disclosure.

In any of the embodiments, the peptide can include structurally similar peptides to those disclosed herein. Structurally similar peptides can encompass variations such as the substitution of one amino acid having a first amino acid side chain with a second amino acid having a second amino acid side chain. Both the first amino acid side chain and the second amino acid side chain provide a similar characteristic to maintain structural similarity. A similar characteristic can include a side chain that has a similar polarity, charge, or size as the first amino acid side chain. As an example, leucine includes a hydrophobic side chain, which could be substituted with an isoleucine, valine, or alanine because each of these amino acids includes a hydrophobic side chain. As another example, histidine includes an aromatic side chain that can also carry a positive charge, which could be substituted with either amino acids that include aromatic side chain or with amino acids that can carry a positive charge such as, phenylalanine, tyrosine, tryptophan, arginine, or lysine. These are provided as examples of possible substitutions and are not meant to limit the scope of variations contemplated by substituting amino acids that have similar side chain properties.

In embodiments of the disclosure, the modification can include an endcap. In some of these embodiments, the endcap may be the only modification to the ordered sequence (e.g., SEQ ID NOs: 18-19). In other embodiments, the endcap can provide a further modification in addition to one or more other modifications as described above.

For embodiments of the disclosure that include an endcap, the endcap can provide a modification to a terminus of the peptide, such as the C-terminus or the N-terminus. Exemplary endcaps include: N-terminal acetylation (Ac—), C-terminal amidation (—$NH_2$), a protecting group, or a protein fusion. Possible protecting groups can include for example: 9-fluorenylmethoxycarbonyl (Fmoc), tert-butyloxycarbonyl (Boc), tert-butyl (t-Bu), trityl (Trt). Possible protein fusions can include: fluorescent tags, purification tags, or delivery sequences. Further, the protein fusions can include a peptide linker such as a glycine linker. Endcap modifications can assist in the delivery of the peptide to a directed site, such as a tumor cell. Endcap modifications can also assist the delivery of the peptide into the cytosol. Endcap modifications could also improve peptide stability or detection in embodiments described herein.

Embodiments of the disclosure can include a peptide having a linear sequence. In these embodiments, the peptide having a linear sequence indicates that no intramolecular bonds exist between two different amino acids from the ordered sequence. As such, a peptide having a linear sequence may include ring structures on individual residues (e.g., SEQ ID NOs: 4-15 include F516 and/or H510). In particular, a peptide may include one or more amino acids, either as a component of the core sequence, as a modification to the starting SEQ ID NO: 1, or as a residual portion of SEQ ID NO: 1 external to a modification that include a side chain ring, such as the amino acids: Histidine, Phenylalanine, Tryptophan, or Tyrosine.

Alternative embodiments of the disclosure include peptides having a cyclic sequence. In these embodiments, the peptide includes an intramolecular bond between two different amino acids. Several non-limiting examples of linkages between side chains of different amino acids that can be used to produce a cyclic sequence can include a disulfide bond, a lactam ring, or a lactone ring.

In an embodiment of the disclosure, the peptide can include one or more cyclic sequences. Peptides that have one or more cyclic sequences can include combinations such as a disulfide bond and a lactam ring or both cyclic sequences can include the same bond.

In some embodiments, the cyclic sequence may be deemed macrocyclic, in that a cyclic sequence of the peptide includes a ring size greater than 4 amino acid residues. In some embodiments, a cyclic sequence can include a ring size greater than 5 residues. In yet other embodiments, a cyclic sequence can include a ring size greater than 8 residues. In still other embodiments, a cyclic sequence can include a ring size greater than 10 residues.

For embodiments of the disclosure of a peptide having a cyclic sequence, in some cases the cyclic sequence can include a ring modification to adjust the ring size. As one example, the substitution of lysine for ornithine results in an additional methylene group on the amino acid side chain. Additional ring modifications can be used to adjust the ring size such as ring closing metathesis to generate an olefin linked bridge, reductive amination to generate a secondary or tertiary amine linked bridge, and ether or thioether bridge formation. To incorporate these ring modifications, the side chains of one or more amino acids may be altered to include a reactive group. Possible reactive groups can include an alkene, a thiol, a hydroxyl, a halogen, and a nitrile.

In an embodiment, a peptide having a cyclic sequence can include an ordered sequence of amino acids corresponding to residues 504-518 from SEQ ID NO: 1 along with a modification, the modification including at least the two amino acid substitutions L505C and F516C and where the cysteine side chains form a disulfide bond to yield a cyclic sequence.

In another embodiment, a peptide having a cyclic sequence can include an ordered sequence of amino acids corresponding to residues 505-519 from SEQ ID NO: 1 along with a modification, the modification including at least the two amino acid substitutions T5080 and I513E and where the ornithine and glutamic acid side chains form a lactam bond to yield a cyclic sequence.

In another embodiment, a peptide having a cyclic sequence can include an ordered sequence of amino acids corresponding to residues 505-519 from SEQ ID NO: 1 along with a modification, the modification including at least the two amino acid substitutions T508K and I513E and where the lysine and glutamic acid side chains form a lactam bond to yield a cyclic sequence.

For some embodiments, the peptide can include a modification to the peptide backbone. In these embodiments, the peptide can be either linear or cyclic. Additionally, the peptide can include an amino acid substitution or an end cap in addition to the modification to the peptide backbone. As an example of the modification to the peptide backbone, the composition can contain a peptide that includes an N-methylation of at least one backbone amide nitrogen. Other modifications can include peptoid derivatives where the amino acid side chain is attached to the amide nitrogen instead of the alpha carbon.

The peptides disclosed herein can be synthesized using standard methods such as solid phase synthesis or an engineered cell line.

Further, the peptides disclosed herein can be included as part of a composition to maintain stability or provide a vehicle for delivery of the peptide. Example compositions having the peptide can also include carriers and/or buffers to maintain the peptide concentrations from about 0.05 µM to about 200 mM.

Embodiments of the disclosure also include methods for inhibiting growth in a target cell, such as a tumor cell, by delivering a peptide as disclosed herein to the tumor. In these embodiments, the method can include delivering a peptide as described herein to a site that contains tumor cells.

In embodiments for inhibiting growth in a tumor, the tumor can be melanoma. In other embodiments, the tumor can be hairy cell leukemia. In further embodiments, the tumor can be colorectal carcinoma. In still further embodiments, the tumor can be astrocytoma. Generally, the tumor types are not limited only to those described above. Embodiments of the disclosure can be used to inhibit growth for tumors that include a mutant Ras genotype and a mutant or a wildtype RAF genotype. Thus, embodiments of the disclosure can be used for tumors lacking the V600E mutation to B-Raf kinase.

As an example of possible Ras mutations, several amino acid positions have been identified in mutant Ras proteins present in tumors. A non-limiting list of amino acid positions for the Ras protein that may be mutant in a tumor or tumor cell using embodiments of the disclosure can include: Gly12, Gly13, and Gln61.

In any of these methods, embodiments of the disclosure can be used to inhibit growth in tumors that have demonstrated resistance to other lines of treatments, including tumors that are resistant to treatment with vemurafenib.

In an embodiment of the disclosure, the method for inhibiting growth in a tumor includes delivering a composition that includes a peptide to a patient using an administration route. In these embodiments, the administration route can include one or more of the following: Intravenous injection, intramuscular injection, oral capsule, sublingual tablet, skin ointment, or anal suppository.

In one embodiment, disclosed peptides can inhibit dimer formation between Raf kinase proteins. By inhibiting dimer formation, the methods provide a mechanism for allosterically blocking kinase function. The method for inhibiting dimer formation including exposing a Raf kinase protein to an embodiment of the composition containing a peptide where the peptide displays a binding affinity ($K_d$) to a region on the Raf kinase protein.

Another embodiment of the disclosure is a method for inhibiting dimer formation between Raf kinase proteins. In some embodiments, the Raf kinase protein can be present in a tumor cell, such as a melanoma cell, a hairy cell leukemia cell, an astrocytoma cell, or a colorectal carcinoma cell. In other embodiments, the Raf kinase protein can be isolated from a cell such that the Raf kinase protein is in solution. In these embodiments, the Raf kinase protein can include B-Raf kinase.

In embodiments of the disclosure that provide a method for inhibiting dimer formation between Raf kinase proteins, the Raf kinase proteins can include a mutation. Mutations are common in cancer cells, and the peptides and compositions described herein can be used to inhibit dimerization between Raf kinase proteins that display a mutation. In an exemplary embodiment, the method for inhibiting dimer formation can include delivering a peptide or a composition containing a peptide to a B-Raf kinase protein. For these embodiments, the B-Raf kinase protein can include a V600E point mutation.

In embodiments of the disclosure, the peptide binding affinity $K_d$ for the dimer interface can be approximately 3.50 µM or less. In certain embodiments, the binding affinity $K_d$ can be approximately 2.00 µM or less. In some embodiments, the binding affinity $K_d$ can be approximately 1.00 µM or less, such as about 0.75, about 0.70, about 0.65, about 0.60, about 0.55, or about 0.50 µM or less. In an exemplary embodiment, the binding affinity $K_d$ can be approximately 0.1 µM or less.

In any of the above embodiments, the peptide may include a REPLACE modification to replace residues in the peptide for non-peptidic analogues. For example, the REPLACE modification could be applied to the residues in the ordered sequence that are not part of the core sequence (i.e., residues that are adjacent to the core sequence). Alternatively, or additionally, the REPLACE modification could be applied to the core sequence. The REPLACE modification utilizes structure-activity relationships to substitute a non-peptide fragment for portions of a peptide inhibitor, as illustrated in U.S. Pat. No. 9,175,357, incorporated in its entirety herein by reference. By utilizing computational analysis, the REPLACE strategy provides a mechanism to identify non-peptide fragments which display similar, improved or diminished binding and/or interactions as the peptide fragment that is being replaced. The fragment can be developed to substantially maintain and mimic the structure activity in an analogous manner to the substitution of an amino acid having a hydrophobic side chain for different amino acid with a hydrophobic side chain, except without being constrained to using an amino acid. Using this method, each potential non-peptide fragment can be scored and thus prioritized through energetic and/or geometric evaluation of computational docking simulations.

Some examples of non-peptide fragments can be found in U.S. Patent Pub. 2017/0283445, incorporated in its entirety herein by reference. Generally, these fragments include an aromatic core that can be heterocyclic and includes at least one substitution to the ring. Other fragments can include secondary or tertiary amines that include an alpha, beta, or gamma carboxyl group.

An exemplary non-peptide fragment can include the following structure, Structure I:

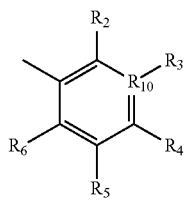

in which $R_2$-$R_6$ are independently selected from hydrogen, carboxyl, alkyl, alkyl ester, hydroxyl, methoxy, halogen, sulfonamide, phosphate, nitro, methylamine, or boronic acid, and $R_{10}$ is C or N, and $R_3$ is relevant only when $R_{10}$ is C.

Several non-limiting structures for non-peptide fragments derived from Structure I are included below as Structures Ia-Id:

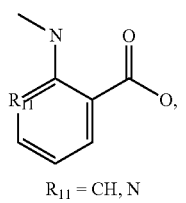
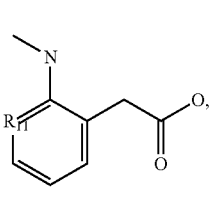
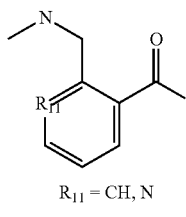
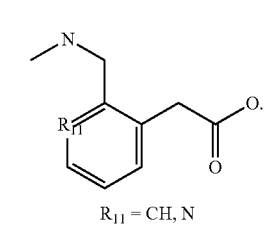

Another exemplary non-peptide fragment can include the following structure, Structure II:

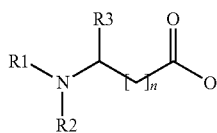

in which R1, R2, and R3 are selected from a hydrogen (H) or an alkyl group having a chain length of 1-3 carbons and n=0-3.

Several non-limiting structures for non-peptide fragments derived from Structure II are included below as Structures IIa-IIb:

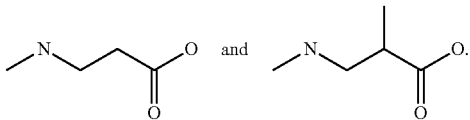

Another exemplary non-peptide fragment can include the following structure, Structure III:

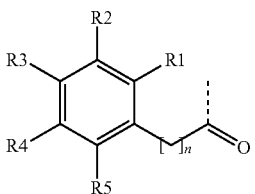

in which R1-R5 can be independently selected from a hydrogen (H) a linear or branched alkyl group having a chain length of 1-5 carbons, an amine, an amide, a carboxylate, a sulfate, a sulfamide, a cyano, or a halogen (e.g., F, Cl, or Br), and n=0-4.

Several non-limiting structures for non-peptide fragments derived from Structure III are included below as Structures IIIa-IIId:

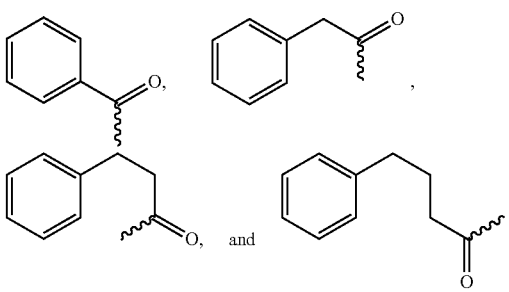

Another exemplary non-peptide fragment can include the following structure, Structure IV:

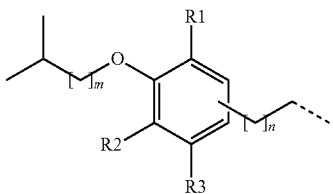

in which R1-R3 can be independently selected from a hydrogen (H) a linear or branched alkyl group having a chain length of 1-5 carbons, an amine, an amide, a carboxylate, a sulfate, a sulfamide, a cyano, or a halogen (e.g., F, Cl, or Br); and the alkyl chain having a chain length, n=0-3, may be positioned on the phenyl ring at any position including ortho, meta, or para, relative to the alkoxy group having a chain length, m=1-3.

Several non-limiting structures for non-peptide fragments derived from Structure IV are included below as Structures IVa-IVc:

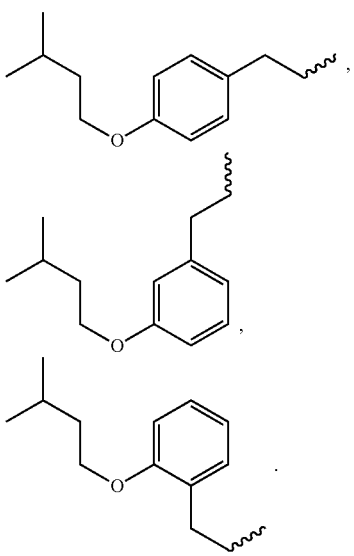

A further example non-peptide fragment that can be incorporated in embodiments of the disclosure can include the following structure, Structure V:

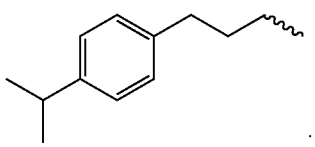

In an example implementation of the REPLACE strategy, SEQ ID NO: 38 can include substituting the sequence of amino acid residues LRK with a non-peptide fragment having the general structure of Structure III. Certain calculations for embodiments using Structures IIIa-IIId are shown in FIG. 12.

Figure 13:
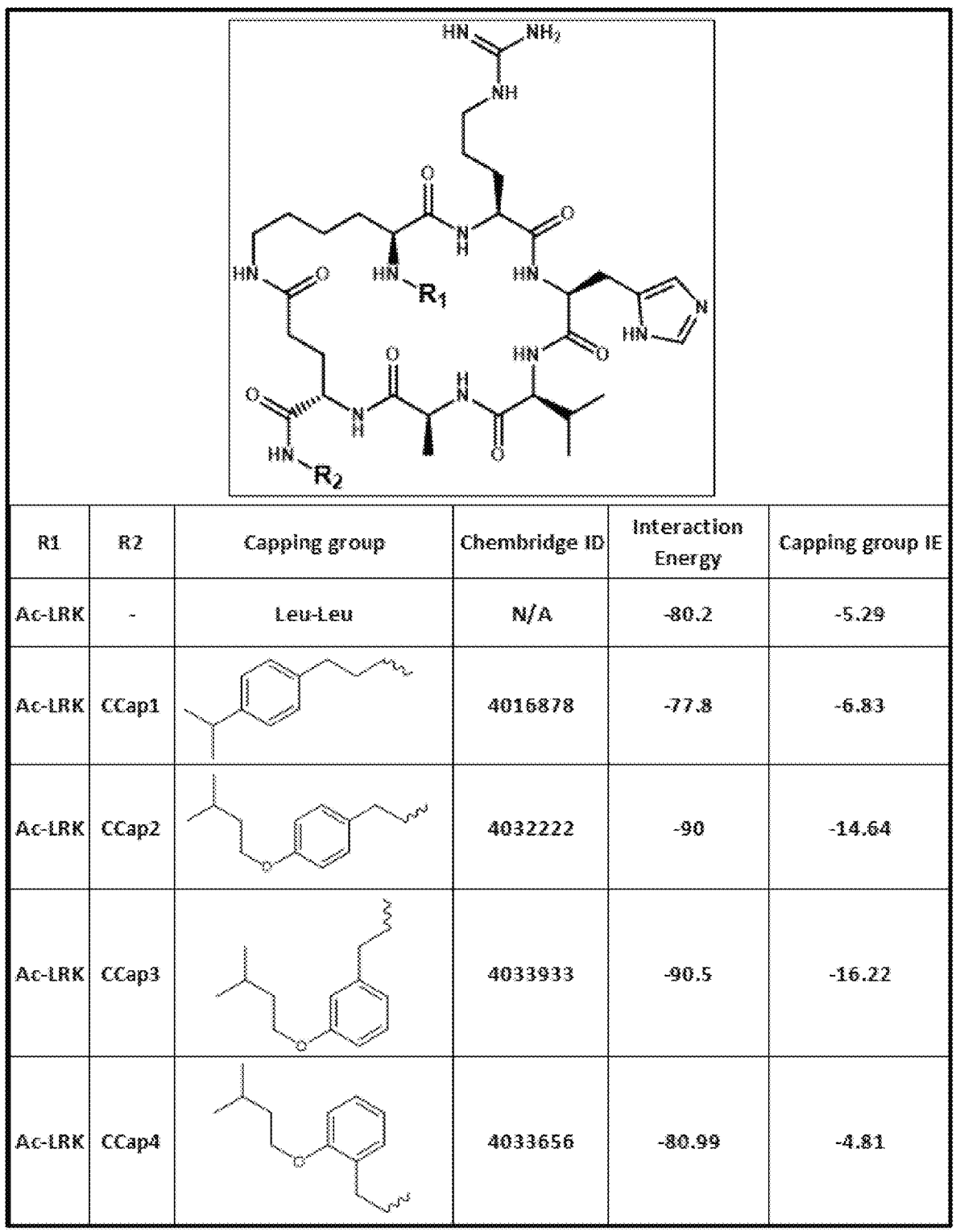
FIG. 13 illustrates arrangements of chemical structures for example peptide-based inhibitors developed using the REPLACE strategy in accordance with example embodiments of the disclosure.

In another example implementation of the REPLACE strategy, SEQ ID NO: 38 can include substituting the sequence of amino acid residues LLFMG (SEQ ID NO: 44) with a non-peptide fragment having the general structure of Structure IV. Certain calculations for embodiments using Structures IVa-IVc are shown in FIG. 13.

Generally, implementations of the REPLACE strategy can be used to replace a single amino acid sequence or may be combined by substituting one or more sequences of amino acids with non-peptide fragments. For example, any embodiment of the disclosure or any of the peptide sequences disclosed herein that include amino acid residues LRK, LLFMG (SEQ ID NO: 44), or both (e.g., SEQ ID NOs: 34, 35, 36, 37, or 38) can include a REPLACE modification to substitute one or both sequences of amino acid residues LRK and LLFMG (SEQ ID NO: 44), respectively, with a first non-peptide fragment having the general structure of Structure III and/or a second non-peptide fragment having the general structure of Structure IV.

As another example implementation of the REPLACE strategy, SEQ ID NO: 31 can include a REPLACE modification to substitute one or both sequences of amino acid residues LRK and LLFMG (SEQ ID NO: 44), respectively, with a first non-peptide fragment having the general structure of Structure III (e.g., Structure IIIa) and a second non-peptide fragment having the general structure of Structure IV (e.g., Structure IVa). Certain attributes, including $K_d$ values, for these peptide-based inhibitors designed in accordance with the disclosure are shown in FIG. 14.

As shown in FIG. 1, peptides as disclosed herein can display a binding affinity to the dimer forming interface of B-Raf. The unmodified starting sequence, SEQ ID NO: 1, displays a $K_d$ of 3.84±0.32. As shown, some peptides exhibit a lower value to about 0.54, (SEQ ID NO: 6) and other peptides exhibited no measurable binding (SEQ ID NO: 2, SEQ ID NO: 9, and SEQ ID NO:14).

FIGS. 2A-2B display Western blot gels demonstrating that the addition of inhibitory peptide (SEQ ID Nos: 1 and 17) to NRASQ61K-mutant SBC12 melanoma cells can reduce downstream signaling of MEK and ERK by lowering the amount of the phosphorylated or activated form of these proteins (pMEK and pERK). In FIG. 2A, cells were electroporated with the BioRad GenePulser XCell™ in the presence of the indicated concentrations of peptide 1. Following recovery at 37° C. for 30 minutes, the cells were treated with 1 µM PLX4032 for 1 hour or DMSO as a vehicle control. Subsequently, the cells were harvested, lysed using RIPA buffer and analyzed by Western blotting using the indicated antibodies. In FIG. 2B, NRAS$^{Q61K}$ mutant human SBC12 melanoma cells were incubated with 3.60 µM of FAM-TAT-Pep6AlaNC3 (control) or FAM-TAT-Pep17 for three days. Four hours prior to harvest, the cells were treated with 1 µM vemurafenib (PLX4032), or the same volume of DMSO as vehicle control. RIPA buffer lysates were subjected to Western blotting using the indicated antibodies. Detection of HSP90 serves as a representative loading control. Note that vemurafenib upregulates the expression and phosphorylation of MEK, ERK, and its target FRA1 in FAM-TAT-Pep6AlaNC3 treated control cells, while this response is not observed in the presence of FAM-TAT-Pep17.

FIG. 3A illustrates the Structure of SEQ ID NO: 38 100 bound to B-Raf 101. The major binding residue R509, small (508-513), and large (505-516, residues replaced with cysteines in peptide SEQ ID NO: 33) cyclization sites are highlighted. Other residues for interaction with B-Raf are labeled including H510, A512 and L515.

FIG. 3B shows the dimer interface, illustrating the interaction between the peptide SEQ ID NO: 38 100 and B-Raf. Peptide residue R509 forms an anti-parallel binding mode with Arg509 (B-Raf) as observed from the crystal structure. It is proposed that the charge-charge repulsion of the two guanidinium groups is offset by the interaction of the positive charge with the negative charge on the C-terminal end of the α-C helix created by the helix dipole. A space filling representation of the ATP competitive kinase inhibitor 102 (from 4E26) indicates the proximity of the dimer forming interface to the catalytic site.

Figure 4:
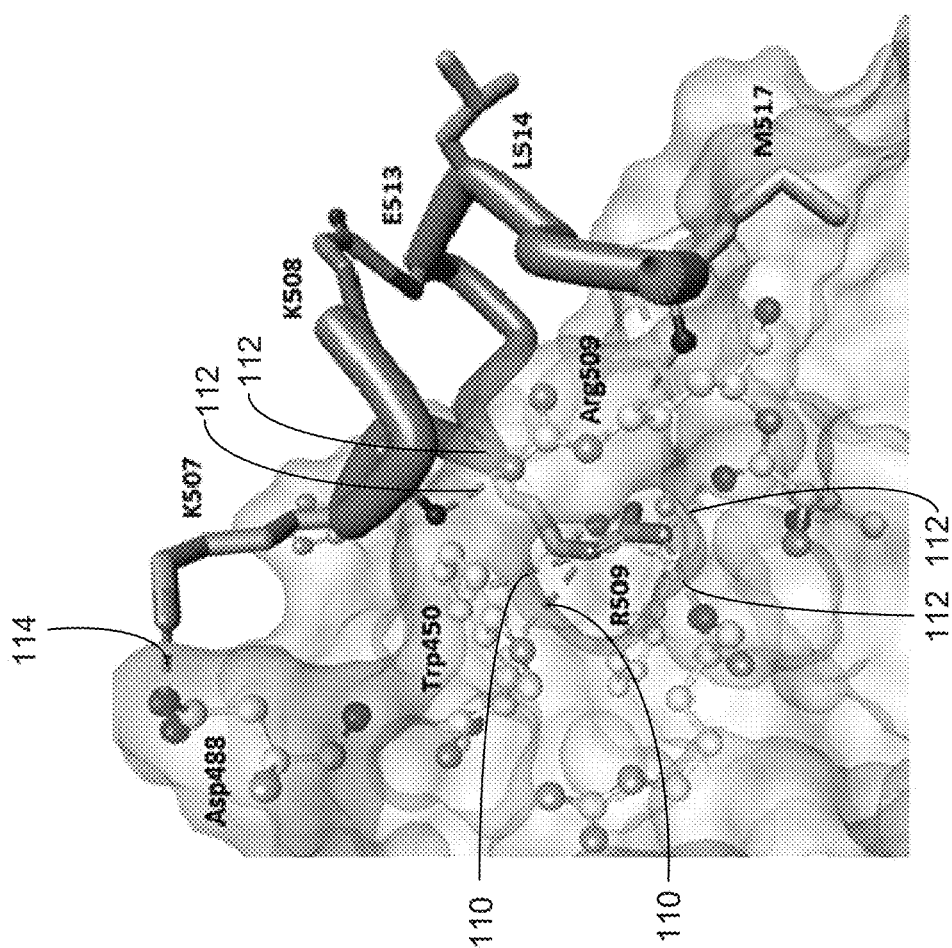
FIG. 4 illustrates some of the binding interactions between residues of an example peptide inhibitor and B-Raf residues.

FIG. 4 illustrates a view of the bound peptide 38 (one letter residue codes) with B-Raf (three letter residue codes) and illustrating some predicted stabilizing non-bonded interactions. The predicted interactions include: Pi-cation 110, H-bond 112 and salt bridge 114, shown as dashed lines.

Figure 5:
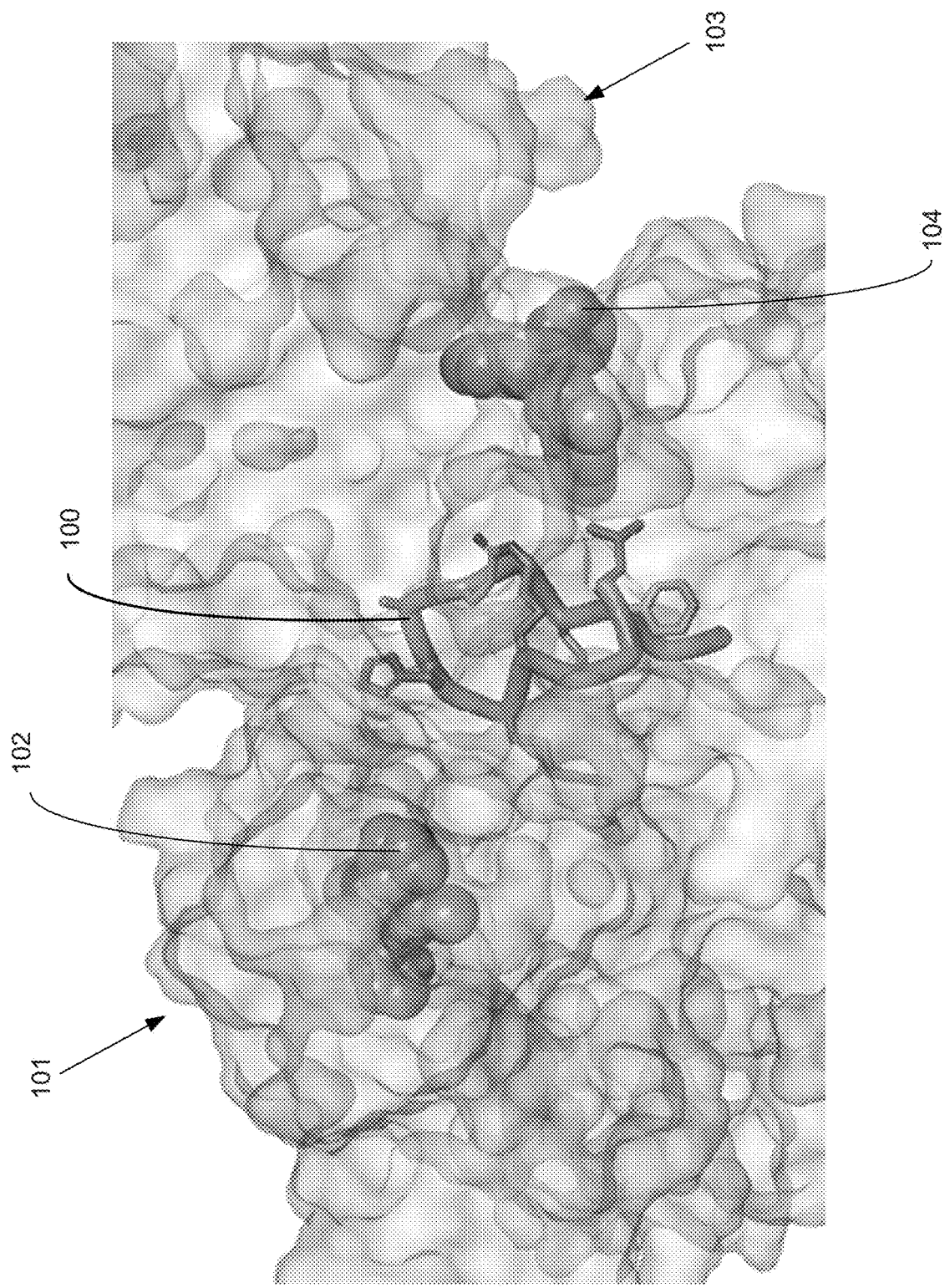
FIG. 5 illustrates the dimeric structure of B-Raf. The macrocyclic dimer interface inhibitor is shown between two B-Raf kinase proteins.

FIG. 5 illustrates a B-Raf kinase protein dimer with SEQ ID NO: 38 100 at the interface. A B-Raf kinase protein 101 is shown with the kinase inhibitor 102, shown as space filled representation. A second B-Raf kinase protein 103 is also shown with a second kinase inhibitor 104.

Figure 6:
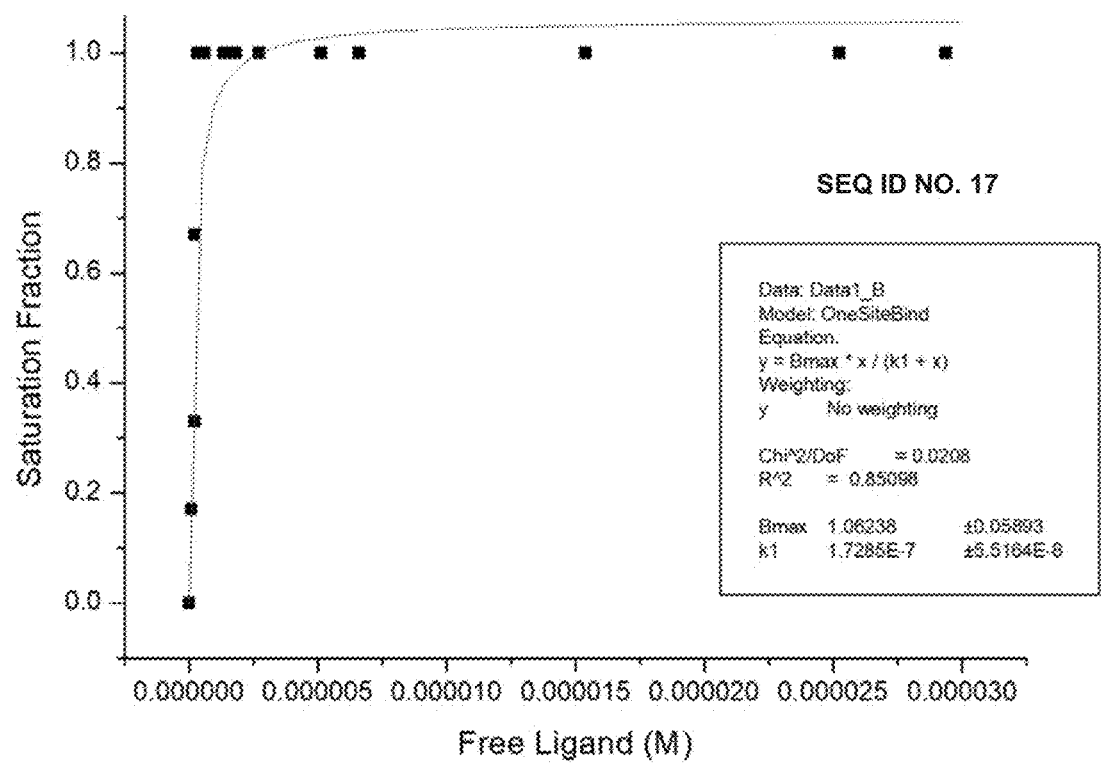
FIG. 6 illustrates a graph displaying saturation fraction versus free ligand (M) using the SEQ ID NO: 17.

FIG. 6 illustrates a graph showing a saturation binding curve obtained for binding of SEQ ID NO: 17 to B-Raf using intrinsic Trp fluorescence.

Figure 7:
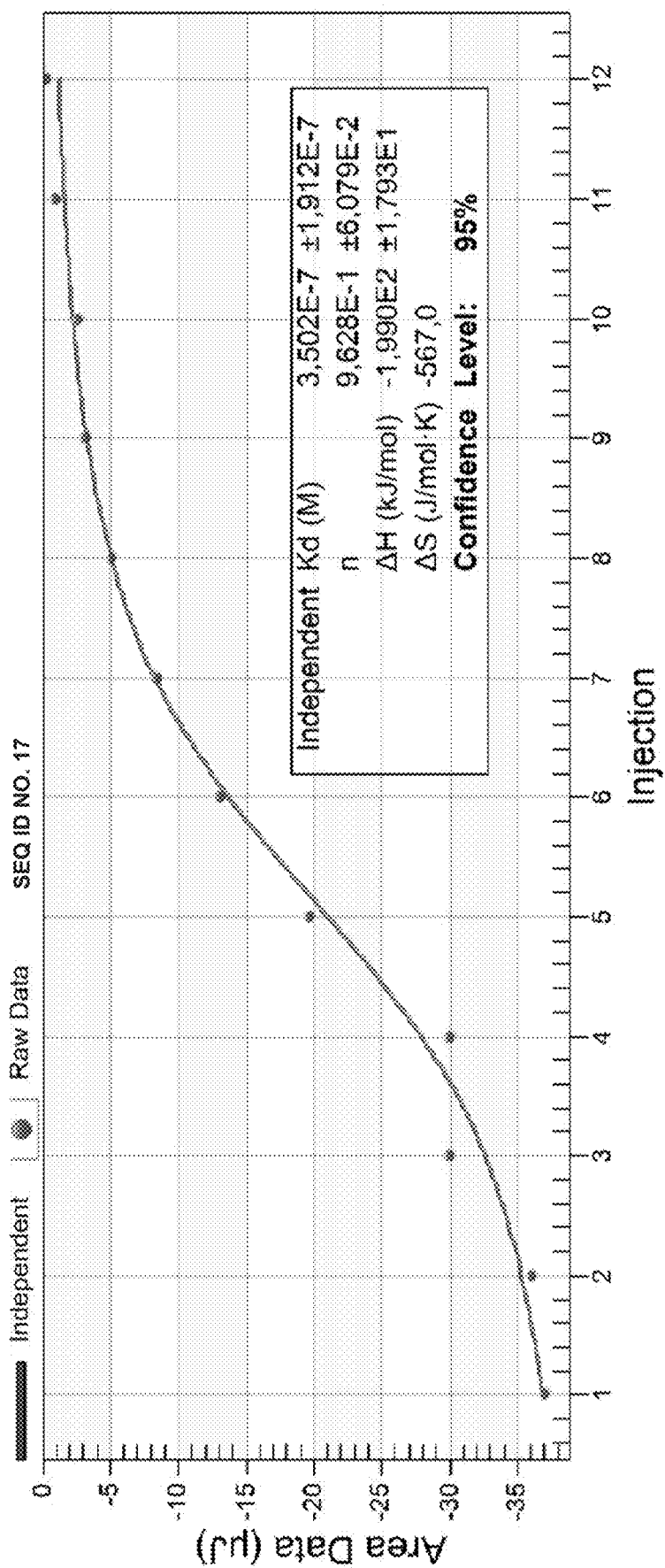
FIG. 7 illustrates a graph of raw data and an independent fit line displaying area data versus injection using SEQ ID NO: 17.

FIG. 7 shows a binding curve for peptide SEQ ID NO: 17 (6097) to B-Raf using Isothermal Titration calorimetry.

As shown in FIG. 8, disclosed peptides can also display a binding affinity for the dimer forming interface. The peptides can include a modification such as an amino acid substitution (SEQ ID NO: 20 through SEQ ID NO: 30) or an endcap (SEQ ID NO: 18, SEQ ID NO:19) to improve or adjust the binding affinity for the dimer forming interface.

FIG. 9 further shows that macrocyclic peptides as disclosed herein can display a binding affinity for the dimer forming interface. The peptides can include at least 2 amino acid substitutions and a side chain bond such as a disulfide bond (SEQ ID NO: 33) or a lactam ring (SEQ ID NO: 34 through SEQ ID NO: 38) to produce the macrocyclic ring.

FIGS. 10a and 10b display tables that indicate LCMS conditions and results for analyzing peptides described in embodiments herein.

Figure 11:
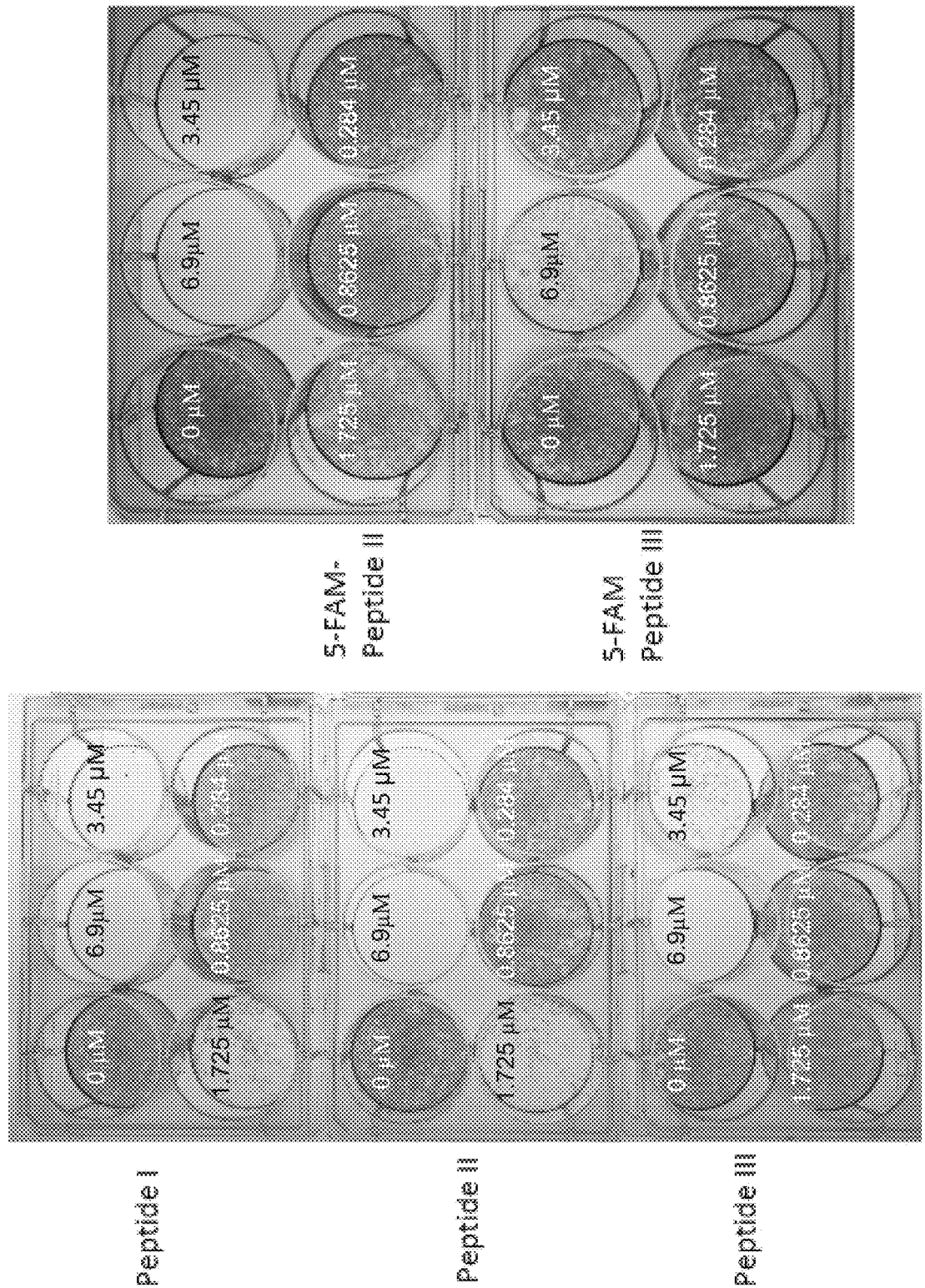
FIG. 11 illustrates images of a well-plate assay using exemplary embodiments of the disclosure.

FIG. 11 illustrates a well plate assay demonstrating the effect of embodiments of the disclosure on the growth of melanoma cells. Several example peptides corresponding to SEQ ID NOs: 1-3 were provided to melanoma cells at concentrations of the peptide inhibitor ranging from 0 μM to about 6.9 μM. In the images, a darker or opaquer well indicates that cell growth is less inhibited, and a lighter or clearer well indicates that cell growth is more inhibited. Going from left to right and top to bottom, the six wells have respective concentrations of: 0 μM, 6.9 μM, 1.725 μM, 0.8625 μM, 0.284 μM.

FIGS. 12 and 13, illustrate data for embodiments that include a non-peptide analog determined using a REPLACE strategy. In FIG. 12, the peptide inhibitor having the sequence corresponding to LRKKRHVNELLFMG (i.e., SEQ ID NO: 37) includes a modification to substitute the non-peptide fragment, shown under the structure heading for the sequence of amino acids LRK. Also shown are the corresponding interaction energy (IE) and capping group IE. For these embodiments, the IE is generally shown to decrease compared to the original peptide (i.e., row 1 having structure Lys), indicating more favorable binding of the modified peptides, though, as shown in the next figure, some capping groups may cause the IE to increase. In FIG. 13, the peptide inhibitor having SEQ ID NO: 37 includes a modification to substitute the non-peptide fragment, shown under the structure heading for the sequence of amino acids LLFMG (SEQ ID NO: 44). As shown, embodiments of the REPLACE modification can include structures that decrease the IE (e.g., Structures IVa-c) and/or structures that increase the interaction energy (e.g., Structure V.) Generally, the more negative the IE, the lower the Kd, and thus, the more tightly bound the modified peptide.

The present disclosure may be better understood with reference to the Methods set forth below in combination with the Drawings.

Methods

Solid Phase Synthesis of Linear Peptides

The synthesis of peptide analogs was accomplished using standard Fmoc chemistry. The linear sequences were synthesized on H-Rink Amide ChemMatrix resin using a Protein Technologies Prelude peptide synthesizer. Initially, the resin was swelled in DMF 3 times followed by 5 min washes. Amino acid coupling reactions were accomplished with Fmoc protected amino acids (4 eq), HATU (4 eq), and DIPEA (8 eq), the reagents were dissolved in DMF (5 mL) and the reaction was mixed via nitrogen bubbling for 2 hours at room temperature. Following coupling, the reaction vessel was drained, and the resin is washed 3× with DMF, 3× with DCM, and 3× with DMF again. For Fmoc deprotection, the resin is treated with a solution of piperidine (20% in DMF) 2×10 minutes. Again, the resin is washed as previously stated and the process is repeated for each respective residue in the defined sequence.

Peptide Cyclization Reactions

Side chain to side chain cyclization was accomplished by one of two methods, either through a lactam linkage or through a disulfide bond linkage. Cyclization residues with orthogonal protecting groups were chosen to be able to selectively deprotect the side chains of specific residues without affecting the rest of the peptide. For the lactam method, the amine residue's side chain was protected with Mtt and the acid residue's side chain was protected with 2-O-PhiPr. Both protecting groups can easily be removed by treatment (7×3 min) of the resin with a low concentration of TFA (2%) in DCM. Once the orthogonal protecting groups have been removed, overnight treatment with HATU (4 eq) and DIPEA (8 eq) was used to effectively cyclize the linear, partially deprotected peptide. For the disulfide cyclized peptides, the cysteine residues involved in the cyclization were orthogonally protected with Mmt, which can easily be removed by treatment (7×3 min) of the resin with a low concentration of TFA (2%) in DCM. Following deprotection, the two cysteine side chains can be oxidized to form the disulfide bridge by treatment with a solution of NCS (2 eq) dissolved in DMF for 15 minutes at room temperature. Following cyclization, peptides are cleaved from the resin by treatment with a solution of TFA/TIPS/H2O (94/5/1) for two hours. The cleavage solution was drained from the synthesis vessel and the solvent evaporated to yield the crude product.

N-Terminal Capped Peptide Synthesis

Peptides were synthesized on H-Rink Amide ChemMatrix resin using standard Fmoc chemistry as previously stated. After the linear sequence is complete, the terminal Fmoc protecting group is removed by treatment (2×10 min) with a solution of piperidine (20% in DMF). Following deprotection, the resin is washed three times each with DMF, DCM, and DMF again. For the addition of the capping group, the resin is treated with a solution of the N-terminal capping group (4 eq), HATU (4 eq), and DIPEA (8 eq) dissolved in DMF for 2 hours while shaking at room temperature. The resin is then washed three times each with DMF and DCM. If the peptide is to be cyclized, that procedure would happen here using methods stated previously, and if not, the peptide is cleaved from the resin as previously stated.

C-Terminal Capped Peptide Synthesis

Peptides were synthesized on 2-chlorotrityl chloride resin using standard Fmoc chemistry as previously stated. After the linear sequence is complete, the peptide is cyclized if need be, then the peptide is cleaved under mild conditions by treatment (2×5 min) with a solution of TFA (1% in DCM). The solution is then collected, and the solvent is removed via evaporation to yield the protected peptide in solution with a free C-terminus carboxylic acid. For the addition of the capping group, the protected peptide is dissolved in DCM and treated with a solution containing the C-terminal capping group (2 eq), HATU (2 eq), and DIPEA (4 eq) all dissolved in DCM and allowed to stir at room temperature overnight. The reaction is ended by evaporation of the solvent and then treatment with a solution of TFA/TIPS/H$_2$O (94:5:1) for 2 hours for the removal of the protecting groups. The solvent is then removed by evaporation and the product is then ready for purification.

Purification of Cyclic Peptides

The crude peptide product was precipitated several times from cold ethyl ether and filtered through a fritted funnel to remove the majority of the scavenged protecting groups. The precipitate is then dissolved in a solution of ACN/MeOH/H$_2$O (1:1:1) and further purified by 200 injections onto a Phenonomex C18 semi-preparative column. Separation is accomplished using a standard water/acetonitrile (0.1% formic acid) mobile phase with a separation gradient of 5-30% B over 40 minutes. Fractions are characterized via mass spectrometry, combined, and purity evaluated by injection on an analytical LCMS column.

Dissociation Constant ($K_d$) Determination from Fluorescence Measurements

The dissociation constant is an indicator of binding strength between two molecules. For the reaction: P+L⇌PL $K_d$ is expressed by Equation 1:

$$K_d=[P][L]/[PL] \quad \text{Eq. 1}$$

where [P] is the concentration of free Protein, [L] is the concentration of free Ligand, and [PL] is the Ligand-bound-Protein. Eq. 1 indicates that $K_d$ is inversely related to the concentration of the Ligand-bound-Protein.

Fluorescence intensity was measured with a Hitachi F-2500 fluorescence spectrophotometer. A 1.6 mL of protein solution (0.5 μM) was placed in a cuvette and equilibrated at 15° C. for 1 hour. After equilibration, small increments (2-15 μL) of the ligand solution were injected in the cuvette. The experiments were performed in 20 mM Hepes buffer (pH 7.5), 10 mM MgCl2, 30 mM NaCl. (For certain ligands that were insoluble in aqueous media, 5-10% DMSO was added to increase ligand solubility). The excitation and emission wavelengths were 274 nm and 304 nm respectively. The slits were set at 10 and 10 nm in the excitation and emission respectively. To determine dilution effect of B-Raf (due to ligand addition) and any fluorescence effect by unbound ligand, a blank sample containing Trp with the same fluorescence signal, was titrated with ligand additions as described above. The sample absorbance was kept below 0.1 to minimize the inner filter effect.

Dissociation constant of B-Raf/Ligand was calculated by fitting data in Eq. 2.

$$[L_{total}] = \frac{2\Theta[P_{total}]}{K_b(-K_{diss} + \sqrt{K_{diss}^2 - 4K_{diss}[P_{total}](\Theta-1)})} + \Theta[P_{total}] \quad \text{Eq. 2}$$

Data were analyzed using Origin 7, using the one site bind function for nonlinear fit.

Isothermal Titration Calorimetry (ITC) of B-Raf Binding of Peptides

As confirmation of binding affinity in an alternate format and to investigate the thermodynamics of binding for peptides to B-Raf, ITC experiments were carried out for three peptides shown to interact with B-Raf through ITF measurements.

An isothermal titration calorimeter composed of two identical cells surrounded by an adiabatic jacket was used to perform ITC measurements. The thermopile/thermocouple circuits were used to detect temperature differences between a reference cell (filled with buffer or water) and a sample cell containing the macromolecule. During an experiment, ligand is titrated into the sample cell in precisely known aliquots, causing heat to be either taken up or evolved (depending on the nature of the reaction). Measurements consist of the time-dependent input of power required to maintain equal temperatures between the sample and reference cells. In an exothermic reaction, the temperature in the sample cell increases upon addition of ligand. This causes the feedback power to the sample cell to be decreased (remember: a reference power is applied to the reference cell) in order to maintain an equal temperature between the two cells. In an endothermic reaction, the opposite occurs; the feedback circuit increases the power in order to maintain a constant temperature (isothermic/isothermal operation). Observations are plotted as the power needed to maintain the reference and the sample cell at an identical temperature against time. As a result, the experimental raw data consists of a series of spikes of heat flow (power), with every spike corresponding to one ligand injection. These heat flow spikes/pulses are integrated with respect to time, giving the total heat exchanged per injection. The pattern of these heat effects as a function of the molar ratio [ligand]/[macromolecule] can then be analyzed to give the thermodynamic parameters of the interaction under study.

Peptide corresponding to SEQ ID NO: 8 (ITF $K_d$=2.8 μM) was measured by ITC ($K_d$=14.9±10.8 μM; ΔH=-34.8 kJ/mol; ΔS=-28.4 J/mol·K). Peptide 17 (ITF $K_d$=0.13 μM) measured by ITC $K_d$=0.35±0.17 μM. For a flexible linear peptide (also for 8) with high entropy in the free state, binding is primarily enthalpy driven (ΔH=-199 kJ/mol) and the entropy term is unfavorable for the overall free energy (ΔS=-567J/mol·K). The cyclic derivative, 36 was measured by ITC ($K_d$=0.31±0.16 μM) as compared with the ITF assay ($K_d$=0.46 Binding of the macrocyclic peptide is driven more by entropic factors than enthalpic (ΔH=-9.41 kJ/mol and ΔS=92.05 J/mol·K).

Tissue Culture

The generation of MCF-10Atet cells, a subline of the human mammary epithelial cell line MCF-10A, was described previously 30. MCF-10Atet cells were grown at 37° C. in a water vapor saturated 5% CO2 atmosphere in conventional tissue culture plastic vessels (Sarstedt, Nürnbrecht, Germany) containing DMEM/F12 medium (PAN-Biotech GmbH, Aidenbach, Germany) supplemented with 5 vol % horse serum (PAA, Colbe, Germany), 1 vol % glutamine (PAN-Biotech GmbH, Aidenbach, Germany), 1 vol % HEPES (PAN-Biotech GmbH, Aidenbach, Germany), 1 vol % penicillin/streptomycin (PAN-Biotech GmbH, Aidenbach, Germany), 250 μg hydrocortisone (Sigma-Aldrich, Munich, Germany), 50 μg choleratoxin (Sigma-Aldrich, Munich, Germany), 10 μg human recombinant epidermal growth factor (R&D Systems, Wiesbaden-Nordenstadt, Germany), and 4.858 mg human recombinant insulin (Actrapid Penfill solution, Novo Nordisk Pharma GmbH, Mainz, Germany). Cells were passaged twice a week or upon reaching confluency and detached by trypsin/EDTA solution. Five hundred cells were plated onto 6 well plates and grown for 24h prior to peptide treatment.

Western Blotting

NRAS$^{Q61K}$-mutant SBC12 melanoma cells were electroporated with the BioRad GenePulser XCell™ in the presence of the indicated concentrations of peptide. Following recovery at 37° C. for 30 minutes, cells were treated with 1 μM PLX4032 for 1 hour or DMSO as a vehicle control. Subsequently, the cells were harvested, lysed using RIPA buffer, and analyzed by Western blotting using the indicated antibodies.

While certain embodiments of the disclosed subject matter have been described using specific terms, such description is for illustrative purposes only, and it is to be understood that changes and variations may be made without departing from the spirit or scope of the subject matter.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill present invention, which is more particularly set forth in the appended claims. In addition, it should be understood the aspects of the various embodiments may be interchanged both in whole or in part. Furthermore, those of ordinary skill in the art will appreciate that the foregoing description is by way of example only and is not intended to limit the invention further described in the appended claims.

What is claimed is:

1. A peptide comprising a modification to B-Raf residues 503-521 (SEQ ID NO: 1), wherein the modification comprises:
   a) deletion of residues G503 and V504 of SEQ ID NO: 1,
   b) deletion of residues Y519, S520, and T521 of SEQ ID NO: 1,
   c) T508K substitution of SEQ ID NO: 1,
   d) N512A substitution of SEQ ID NO: 1, and
   e) I513E substitution of SEQ ID NO: 1; and
wherein the peptide includes no more than 14 amino acid residues.

2. The peptide of claim 1, wherein the modification further comprises at least 1 additional amino acid substitution.

3. The peptide of claim 1, wherein the modification further comprises an additional 2 amino acid substitutions.

4. The peptide of claim 1, wherein the modification further comprises addition of an endcap to the peptide.

5. The peptide of claim 4, wherein the endcap comprises at least one of the group consisting of: N-terminal acetylation, C-terminal amidation, a protecting group, and a protein fusion.

6. The peptide of claim 1, wherein the modification further comprises one or more of the following substitutions: L505A, H510F, V511A, L514A, L515I, L515 homoleucine, and F516D.

7. The peptide of claim 1, wherein the modification further comprises one or more of the following substitutions: L505C, H510H(d), H510V, H510L, F516C, M517S, M517T, and M517N, and wherein the peptide comprises a disulfide bond or a lactam ring.

8. The peptide of claim 1, wherein the modification further comprises an ornithine amino acid substitution and a glutamic acid amino acid substitution and wherein the peptide comprises a lactam ring.

9. The peptide of claim 1, wherein the peptide comprises a cyclic peptide sequence.

10. The peptide of claim 1, wherein the peptide is macrocyclic.

11. The peptide of claim 1, wherein the modification further comprises substitution of an L-isomer of an amino acid residue of the peptide sequence with a D-isomer of the amino acid of the peptide sequence.

12. The peptide of claim 1, wherein the modification further comprises N-methylation of a backbone amide nitrogen of the peptide.

13. The peptide of claim 1, wherein the modification further comprises replacement of residues L505, R506, and K507 with a non-peptide fragment.

14. The peptide of claim 13, wherein the non-peptide fragment is selected from

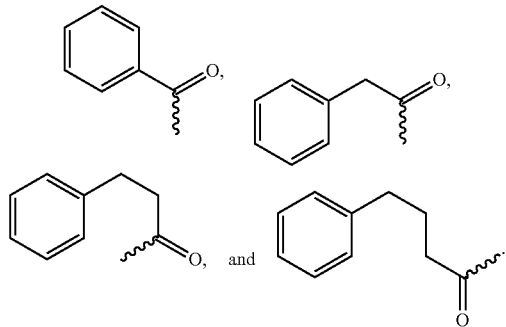

15. The peptide of claim 1, wherein the modification further comprises replacement of residues L514, L515, or F516 with a non-peptide fragment.

16. The peptide of claim 15, wherein the non-peptide fragment is selected from

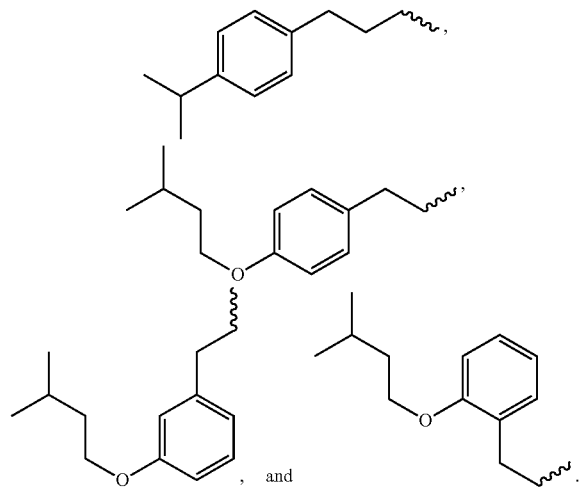

17. A method for inhibiting growth in a tumor comprising delivering the peptide of claim 1 to the tumor.

18. The method of claim 17, wherein the tumor comprises of one or more of the group consisting of: melanoma, hairy cell leukemia, astrocytoma, and colorectal carcinoma.

19. The method of claim 17 wherein the tumor is resistant to treatment with vemurafenib, dabrafenib, trametinib, or combinations thereof.

20. The method of claim 17, wherein delivering the peptide comprises administering a composition comprising the peptide to a patient having the tumor.

* * * * *

SEQUENCE LISTING

<160> NUMBER OF SEQ ID NOS: 46

<210> SEQ ID NO 1
<211> LENGTH: 19
<212> TYPE: PRT
<213> ORGANISM: Unknown
<220> FEATURE:
<223> OTHER INFORMATION: Description of Unknown:
      B-Raf sequence

<400> SEQUENCE: 1

Gly Val Leu Arg Lys Thr Arg His Val Asn Ile Leu Leu Phe Met Gly
1               5                   10                  15

Tyr Ser Thr

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Val Leu Arg Lys Thr His His Val Asn Ile Leu Gly Phe Trp Gly
1               5                   10                  15

Tyr Ser Thr

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Arg Ile Asn Lys Gly Arg His Thr Phe Leu Leu Val Val Met Thr
1               5                   10                  15

Tyr Ser Leu

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Val Ala Arg Lys Thr Arg His Val Asn Ile Leu Leu Phe Met Gly
1               5                   10                  15

Tyr Ser Thr

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Val Leu Glu Lys Thr Arg His Val Asn Ile Leu Leu Phe Met Gly
1               5                   10                  15

Tyr Ser Thr

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Val Leu Leu Lys Thr Arg His Val Asn Ile Leu Leu Phe Met Gly
1               5                   10                  15

Tyr Ser Thr

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Val Leu Arg Lys Asp Arg His Val Asn Ile Leu Leu Phe Met Gly
1               5                   10                  15

Tyr Ser Thr

<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Val Leu Arg Lys Ala Arg His Val Asn Ile Leu Leu Phe Met Gly
1               5                   10                  15

Tyr Ser Thr

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Val Leu Arg Lys Thr Arg Phe Val Asn Ile Leu Leu Phe Met Gly
1               5                   10                  15

Tyr Ser Thr

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Val Leu Arg Lys Thr Arg His Ala Asn Ile Leu Leu Phe Met Gly

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Gly Val Leu Arg Lys Thr Arg His Val Asn Ile Ala Leu Phe Met Gly
1               5                   10                  15

Tyr Ser Thr

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Gly Val Leu Arg Lys Thr Arg His Val Asn Ile Leu Ile Phe Met Gly
1               5                   10                  15

Tyr Ser Thr

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (13)..(13)
<223> OTHER INFORMATION: His or Leu

<400> SEQUENCE: 13

Gly Val Leu Arg Lys Thr Arg His Val Asn Ile Leu Xaa Phe Met Gly
1               5                   10                  15

Tyr Ser Thr

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

Gly Val Leu Arg Lys Thr Arg His Val Asn Ile Leu Leu Asp Met Gly
1               5                   10                  15

Tyr Ser Thr

<210> SEQ ID NO 15
<211> LENGTH: 16
<212> TYPE: PRT
<213> ORGANISM: Unknown
<220> FEATURE:
<223> OTHER INFORMATION: Description of Unknown:

B-Raf sequence

<400> SEQUENCE: 15

Gly Val Leu Arg Lys Thr Arg His Val Asn Ile Leu Leu Phe Met Gly
1               5                   10                  15

<210> SEQ ID NO 16
<211> LENGTH: 14
<212> TYPE: PRT
<213> ORGANISM: Unknown
<220> FEATURE:
<223> OTHER INFORMATION: Description of Unknown:
      B-Raf sequence

<400> SEQUENCE: 16

Val Leu Arg Lys Thr Arg His Val Asn Ile Leu Leu Phe Met
1               5                   10

<210> SEQ ID NO 17
<211> LENGTH: 15
<212> TYPE: PRT
<213> ORGANISM: Unknown
<220> FEATURE:
<223> OTHER INFORMATION: Description of Unknown:
      B-Raf sequence

<400> SEQUENCE: 17

Val Leu Arg Lys Thr Arg His Val Asn Ile Leu Leu Phe Met Gly
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Val Leu Arg Lys Thr Arg His Val Asn Ile Leu Leu Phe Met Gly
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Val Leu Arg Lys Thr Arg His Val Asn Ile Leu Leu Phe Met Gly
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: His or Leu

<400> SEQUENCE: 20

Val Leu Arg Lys Thr Arg His Val Asn Ile Leu Xaa Phe Met Gly

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Ala Arg Lys Thr Arg His Val Asn Ile Leu Leu Phe Met Gly
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Val Leu Ala Lys Thr Arg His Val Asn Ile Leu Leu Phe Met Gly
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Val Leu Arg Ala Thr Arg His Val Asn Ile Leu Leu Phe Met Gly
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Val Leu Arg Lys Thr Ala His Val Asn Ile Leu Leu Phe Met Gly
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Val Leu Arg Lys Thr Arg Ala Val Asn Ile Leu Leu Phe Met Gly
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Val Leu Arg Lys Thr Arg His Val Ala Ile Leu Leu Phe Met Gly
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Val Leu Arg Lys Thr Arg His Val Asn Ala Leu Leu Phe Met Gly
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Val Leu Arg Lys Thr Arg His Val Asn Ile Ala Leu Phe Met Gly
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Val Leu Arg Lys Thr Arg His Val Asn Ile Leu Leu Ala Met Gly
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Val Leu Arg Lys Thr Arg His Val Asn Ile Leu Leu Phe Ala Gly
1               5                   10                  15

<210> SEQ ID NO 31
<211> LENGTH: 14
<212> TYPE: PRT
<213> ORGANISM: Unknown
<220> FEATURE:
<223> OTHER INFORMATION: Description of Unknown:
      B-Raf sequence

<400> SEQUENCE: 31

Leu Arg Lys Thr Arg His Val Asn Ile Leu Leu Phe Met Gly
1               5                   10

<210> SEQ ID NO 32

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Leu Lys Thr Arg His Val Asn Ile Leu Leu Phe Met Gly
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Val Cys Arg Lys Thr Arg His Val Asn Ile Leu Leu Cys Met
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ornithine

<400> SEQUENCE: 34

Leu Arg Lys Xaa Arg His Val Ala Glu Leu Leu Phe Met Gly
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ornithine

<400> SEQUENCE: 35

Leu Arg Lys Xaa Arg His Val Asn Glu Leu Leu Phe Met Gly
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ornithine

<400> SEQUENCE: 36

Leu Arg Lys Xaa Arg His Val Ala Glu Leu Leu Phe Met Gly
1               5                   10
```

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Arg Lys Lys Arg His Val Asn Glu Leu Leu Phe Met Gly
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Arg Lys Lys Arg His Val Ala Glu Leu Leu Phe Met Gly
1               5                   10

<210> SEQ ID NO 39
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Gly Val Leu Glu Lys Thr Arg His Val Asn Ile Leu Leu Phe Met
1               5                   10                  15

Gly Tyr Ser Thr
            20

<210> SEQ ID NO 40
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Ala Val Leu Glu Lys Thr Arg His Val Asn Ile Leu Leu Phe Met
1               5                   10                  15

Gly Tyr Ser Thr
            20

<210> SEQ ID NO 41
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Val Leu Glu Lys Thr Arg His Val Asn Ile Leu Leu Phe Met Gly
1               5                   10                  15

Tyr Ser Thr Ala
            20

<210> SEQ ID NO 42
<211> LENGTH: 12
<212> TYPE: PRT
<213> ORGANISM: Unknown
<220> FEATURE:
<223> OTHER INFORMATION: Description of Unknown:
      B-Raf sequence

<400> SEQUENCE: 42

Lys Thr Arg His Val Asn Ile Leu Leu Phe Met Gly
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys Arg His Val Asn Leu Leu Phe Met Gly
1               5                   10

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Leu Phe Met Gly
1               5

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Arg His Val Asn Ile Leu Leu Phe Met Gly
1               5                   10

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Arg Lys Thr Arg His Val Asn Ile
1               5